(12) United States Patent
Kraft et al.

(10) Patent No.: US 11,192,083 B2
(45) Date of Patent: Dec. 7, 2021

(54) FLOW CELLS WITH CHAMBERS, DEPRESSIONS, AND CAPTURE SITES

(71) Applicant: ILLUMINA, INC., San Diego, CA (US)

(72) Inventors: Lewis J. Kraft, San Diego, CA (US); Tarun Kumar Khurana, Freemont, CA (US); Yir-Shyuan Wu, Albany, CA (US); Xi-Jun Chen, San Carlos, CA (US); Arnaud Rival, Saint Nazaire les Eymes (FR); Justin Fullerton, San Diego, CA (US); M. Shane Bowen, Encinitas, CA (US); Hui Han, San Diego, CA (US); Jeffrey S. Fisher, San Diego, CA (US); Yasaman Farshchi, San Francisco, CA (US); Mathieu Lessard-Viger, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 16/750,831

(22) Filed: Jan. 23, 2020

(65) Prior Publication Data
US 2020/0238247 A1 Jul. 30, 2020

Related U.S. Application Data

(60) Provisional application No. 62/798,348, filed on Jan. 29, 2019.

(51) Int. Cl.
*B01J 19/00* (2006.01)
*C12N 15/10* (2006.01)
(Continued)

(52) U.S. Cl.
CPC ......... *B01J 19/0046* (2013.01); *B01L 3/5027* (2013.01); *B01L 3/502707* (2013.01);
(Continued)

(58) Field of Classification Search
CPC ...... G01N 2021/058; B01J 2219/00313; B01J 19/0046; B01J 2219/00286;
(Continued)

(56) References Cited

U.S. PATENT DOCUMENTS

| | | | | |
|---|---|---|---|---|
| 6,682,702 B2* | 1/2004 | Barth | ................... | G01N 35/028 422/430 |
| 6,893,816 B1* | 5/2005 | Beattie | ................ | B01J 19/0046 422/68.1 |

(Continued)

FOREIGN PATENT DOCUMENTS

| | | |
|---|---|---|
| EP | 1163052 | 6/2010 |
| WO | 2000/07022 | 2/2000 |

(Continued)

OTHER PUBLICATIONS

Bae, et al., "Hydrogel-encapsulated 3D microwell array for neuronal differentiation", Biomedical Materials, vol. 11, Article No. 015019, 2016, pp. 1-8.

(Continued)

*Primary Examiner* — Michael P LaPage
(74) *Attorney, Agent, or Firm* — Illumina, Inc.

(57) ABSTRACT

An example of a flow cell includes a substrate, a plurality of chambers defined on or in the substrate, and a plurality of depressions defined in the substrate and within a perimeter of each of the plurality of chambers. The depressions are separated by interstitial regions. Primers are attached within each of the plurality of depressions, and a capture site is located within each of the plurality of chambers.

16 Claims, 15 Drawing Sheets

(51) Int. Cl.
*C40B 40/08* (2006.01)
*B01L 3/00* (2006.01)
*C40B 50/18* (2006.01)
*C08L 37/00* (2006.01)
*G01N 21/05* (2006.01)

(52) U.S. Cl.
CPC .......... *C12N 15/1065* (2013.01); *C40B 40/08* (2013.01); *C40B 50/18* (2013.01); *B01J 2219/00286* (2013.01); *B01J 2219/00608* (2013.01); *B01L 2300/0877* (2013.01); *C08L 37/00* (2013.01); *G01N 2021/058* (2013.01)

(58) Field of Classification Search
CPC .... B01J 2219/00608; B01J 2219/00511; B01J 2219/00637; B01J 2219/00648; B01J 2219/00722; B01J 2219/00317; B01J 2219/005; B01L 2200/12; B01L 2200/16; B01L 2300/0893; B01L 3/502707; B01L 3/5027; B01L 2300/0877; C12N 15/1065; C40B 40/08; C40B 50/18; C08L 37/00; C08F 220/56

See application file for complete search history.

(56) References Cited

U.S. PATENT DOCUMENTS

| | | | |
|---|---|---|---|
| 9,683,230 | B2 | 6/2017 | Gormley et al. |
| 2005/0277125 | A1* | 12/2005 | Benn .................. B01J 19/0046 435/6.11 |
| 2009/0239759 | A1* | 9/2009 | Balch .................. G01N 35/028 506/9 |
| 2010/0111768 | A1 | 5/2010 | Banerjee et al. |
| 2010/0129822 | A1 | 5/2010 | Siva et al. |
| 2010/0303686 | A1* | 12/2010 | Horiuchi ............. B01L 3/50273 422/400 |
| 2011/0126929 | A1* | 6/2011 | Velasquez-Garcia ....................... H01M 8/04201 137/561 R |
| 2011/0244448 | A1 | 10/2011 | Shirai et al. |
| 2012/0316086 | A1 | 12/2012 | Lin et al. |
| 2013/0225421 | A1 | 8/2013 | Li et al. |
| 2014/0079923 | A1 | 3/2014 | George et al. |
| 2014/0378349 | A1 | 12/2014 | Hindson et al. |
| 2015/0038373 | A1* | 2/2015 | Banyai .................. C12N 15/74 506/16 |
| 2015/0176071 | A1 | 6/2015 | Fisher et al. |
| 2016/0023208 | A1 | 1/2016 | Fisher et al. |
| 2016/0318017 | A1* | 11/2016 | Eltoukhy ............. C12Q 1/6869 |
| 2017/0130260 | A1 | 5/2017 | Rigatti et al. |
| 2018/0149574 | A1 | 5/2018 | Kawamoto et al. |
| 2018/0155709 | A1 | 6/2018 | Gormley et al. |
| 2018/0245069 | A1 | 8/2018 | DeSantis et al. |
| 2018/0245142 | A1 | 8/2018 | So et al. |
| 2018/0273933 | A1 | 9/2018 | Gunderson et al. |

FOREIGN PATENT DOCUMENTS

| | | |
|---|---|---|
| WO | 2010/003132 | 1/2010 |
| WO | 2010/132795 A2 | 11/2010 |
| WO | 2012/170936 | 12/2012 |
| WO | 2013/063382 A2 | 5/2013 |
| WO | 2014/133905 A1 | 9/2014 |
| WO | 2015/138648 A1 | 9/2015 |
| WO | WO 2016/061517 | 4/2016 |
| WO | 2016/075204 A1 | 5/2016 |
| WO | 2016/094512 | 6/2016 |
| WO | WO 2017/201198 | 11/2017 |
| WO | 2018/119101 | 6/2018 |
| WO | WO 2018/119053 | 6/2018 |
| WO | WO 2018/125982 | 7/2018 |
| WO | 2018/208561 | 11/2018 |
| WO | 2019/028047 | 2/2019 |
| WO | 2019/126040 A1 | 6/2019 |
| WO | 2019/160820 | 8/2019 |

OTHER PUBLICATIONS

Neto, et al., "Fabrication of Hydrogel Particles of Defined Shapes Using Superhydrophobic-Hydrophilic Micropatterns", Advanced Materials, vol. 28, 2016, pp. 7613-7619.

Qi, et al., "DNA-directed self-assembly of shape-controlled hydrogels", Nature Communications, vol. 4, Article No. 2275, Sep. 9, 2013, pp. 1-10.

Wang, et al., "How to Construct DNA Hydrogels for Environmental Applications: Advanced Water Treatment and Environmental Analysis", Small, vol. 14, Article No. 1703305, 2018, pp. 1-19.

* cited by examiner

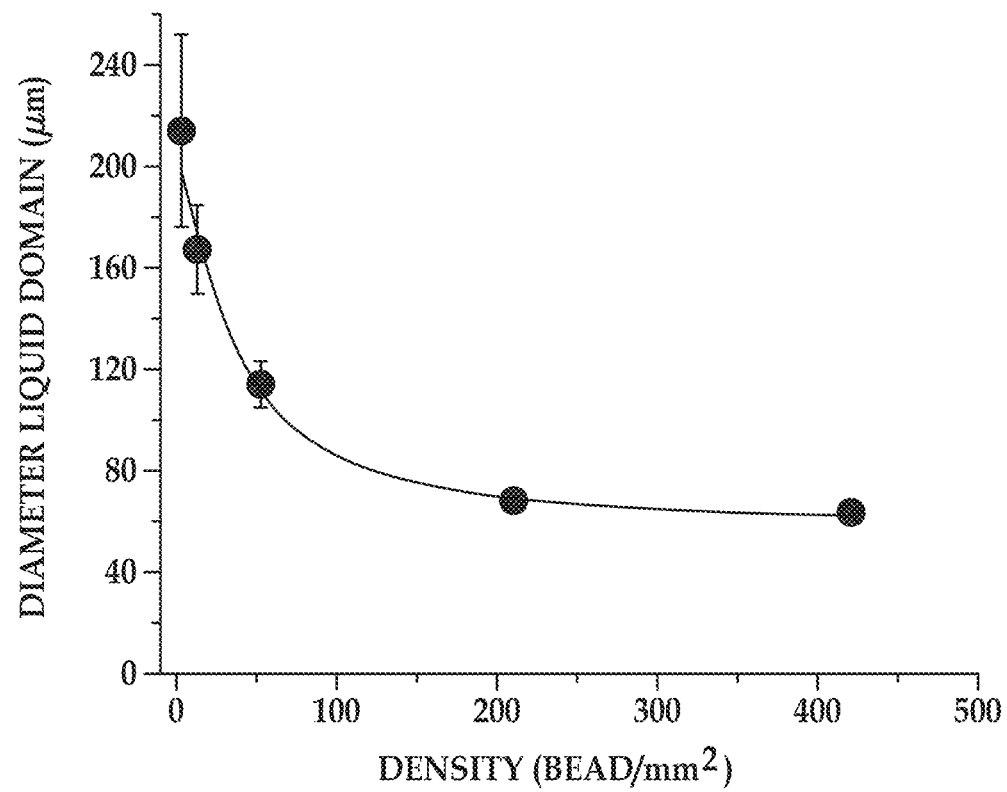
FIG. 13
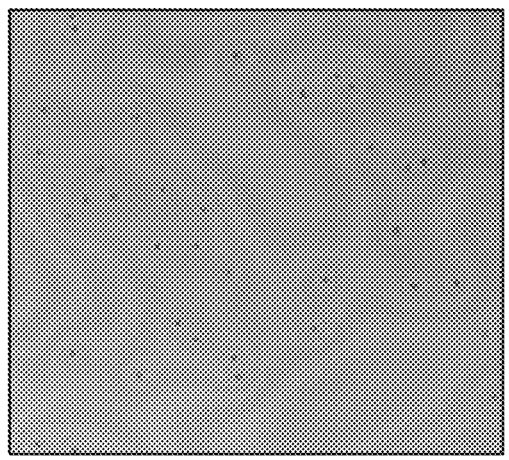
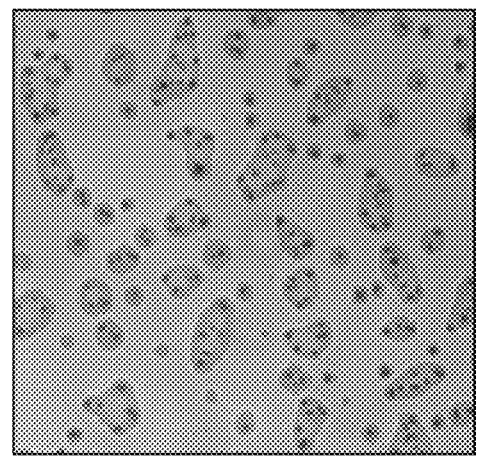
FIG. 14A  FIG. 14B

FLOW CELLS WITH CHAMBERS, DEPRESSIONS, AND CAPTURE SITES

CROSS-REFERENCE TO RELATED APPLICATION

This application claims the benefit of U.S. Provisional Application Ser. No. 62/798,348, filed Jan. 29, 2019; the content of which is incorporated by reference herein in its entirety.

BACKGROUND

There are a variety of methods and applications for which it is desirable to generate a library of fragmented and tagged DNA molecules from double-stranded DNA (dsDNA) target molecules. Often, the purpose is to generate smaller DNA molecules (e.g., DNA fragments) from larger dsDNA molecules for use as templates in DNA sequencing reactions. The templates may enable short read lengths to be obtained. During data analysis, overlapping short sequence reads can be aligned to reconstruct the longer nucleic acid sequences. In some instances, pre-sequencing steps (such as barcoding of particular nucleic acid molecules) can be used to simplify the data analysis.

INTRODUCTION

A first aspect disclosed herein is a flow cell comprising: a substrate; a plurality of chambers defined on or in the substrate; a plurality of depressions defined in the substrate and within a perimeter of each of the plurality of chambers, wherein the depressions are separated by interstitial regions; primers attached within each of the plurality of depressions; and a capture site located within each of the plurality of chambers.

In an example of the first aspect, the capture site is a well that is defined in the substrate, wherein the well has an opening dimension that is larger than an opening dimension of each of the plurality of depressions. In one example, the flow cell further comprises a chemical capture agent within the well. In another example, the flow cell further comprises a capture bead within the well, wherein the capture bead is coated with a chemical capture agent.

In an example of the first aspect, the capture site is a protrusion having a chemical capture agent on a surface thereof.

In an example of the first aspect, the capture site includes a chemical capture agent positioned on a portion of the interstitial regions.

In an example of the first aspect, the flow cell further comprises a hydrophobic material positioned on the substrate, wherein the hydrophobic material defines each of the plurality of chambers.

In an example of the first aspect, each of the plurality of chambers has a height sufficient to block lateral diffusion of released library fragments between adjacent chambers.

In an example of the first aspect, the flow cell further comprises a polymer layer in each of the depressions, and wherein the primers are attached to the polymer layer In an example of the first aspect, each of the plurality of chambers has an opening dimension ranging from about 1 µm to about 1000 µm; each of the plurality of depressions has an opening dimension ranging from about 1 nm to about 2 µm; and the chamber opening dimension is greater than the depression opening dimension.

In an example of the first aspect, the plurality of chambers is arranged in a first pattern across the substrate; and respective sub-sets of the plurality of depressions are arranged in a second pattern within in each of the chambers.

In an example of the first aspect, the plurality of chambers is patterned into the substrate.

It is to be understood that any features of the flow cell disclosed herein may be combined together in any desirable manner and/or configuration.

A second aspect disclosed herein is a method comprising introducing a plurality of complexes to a flow cell including: a plurality of chambers; a plurality of depressions within each of the plurality of chambers; primers attached within each of the plurality of depressions; and a capture site in each of the plurality of chambers; wherein each of the complexes includes: a carrier; and sequencing-ready nucleic acid fragments attached to or contained within the carrier; whereby one of the complexes attaches to a respective one of the capture sites in at least some of the plurality of chambers; and causing the carrier of each complex to release the sequencing-ready nucleic acid fragments therefrom, whereby walls of the respective chambers restrict transport and seeding of the sequencing-ready nucleic acid fragments to respective depressions within each of the respective chambers.

It is to be understood that any features of this method may be combined together in any desirable manner. Moreover, it is to be understood that any combination of features of this method and/or of the flow cell may be used together, and/or combined with any of the examples disclosed herein.

A third aspect disclosed herein is a method comprising introducing a plurality of complexes to a flow cell including: a plurality of chambers, each having a depth that is at least about 50% of an average diameter of the complexes; and primers attached within each of the plurality of chambers; wherein each of the plurality of complexes includes: a carrier; and sequencing-ready nucleic acid fragments from the same template nucleic acid attached to or contained within the carrier; whereby at least some of the complexes become trapped in at least some of the plurality of chambers; washing away non-trapped complexes from the flow cell; and without introducing an external immobilizing agent to the flow cell, causing the carrier of the trapped complexes to release the sequencing-ready nucleic acid fragments into the respective chamber in which each complex is trapped, whereby transport and seeding of the sequencing-ready nucleic acid fragments are restricted by the depth.

In an example of the third aspect, the depth is about 10 µm or more.

In an example of the third aspect, each chamber has a bottom surface, and one of: the primers are attached to a polymer layer across the bottom surface; or the primers are respectively attached to a plurality of spatially segregated polymer islands positioned on the bottom surface.

In an example of the third aspect, each chamber has a bottom surface and a plurality of depressions defined therein, and the primers are respectively attached to a polymer layer within each of the depressions.

In an example of the third aspect, the carrier is a solid support, and wherein the causing involves introducing a cleavage agent to the flow cell or heating the flow cell above an annealing temperature of a first sequence of the sequencing-ready nucleic acid fragments.

In an example of the third aspect, the carrier is a hydrogel support, and wherein the causing involves heating the flow cell, introducing a cleaving agent to the flow cell, or combinations thereof.

It is to be understood that any features of this method may be combined together in any desirable manner. Moreover, it is to be understood that any combination of features of any of the methods and/or of the flow cell may be used together, and/or combined with any of the examples disclosed herein.

A fourth aspect disclosed herein is a method comprising introducing a plurality of complexes to a flow cell including: a plurality of chambers, each having a depth that is about 5 µm or less; a capture site within each of the plurality of chambers; and primers attached within each of the plurality of chambers; wherein each of the plurality of complexes includes: a carrier bead; and sequencing-ready nucleic acid fragments from the same template nucleic acid attached to the carrier bead; whereby at least some of the complexes become immobilized at respective capture sites; washing away non-immobilized complexes from the flow cell; introducing an external immobilizing agent to the plurality of chambers; and causing the carrier bead of the trapped complexes to release the sequencing-ready nucleic acid fragments into the respective chamber in which each complex is trapped, whereby transport and seeding of the sequencing-ready nucleic acid fragments are restricted by the external immobilizing agent.

In an example of the fourth aspect, the external immobilizing agent is a gaseous diffusion barrier; a liquid diffusion barrier selected from the group consisting of mineral oil and silicone oil; a viscous medium diffusion barrier selected from the group consisting of glycerol and sucrose; or combinations thereof.

In an example of the fourth aspect, the capture site is a capture site primer, and wherein each of the complexes includes a complementary primer that can hybridize to the capture site primer.

In an example of the fourth aspect, the capture site includes a first member of a binding pair and wherein each of the complexes includes a second member of the binding pair.

In an example of the fourth aspect, each chamber has a bottom surface, and one of: the primers are attached to a polymer layer across the bottom surface; or the primers are respectively attached to a plurality of spatially segregated polymer islands positioned on the bottom surface.

In an example of the fourth aspect, each chamber has a bottom surface and a plurality of depressions defined therein, and wherein the primers are respectively attached to a polymer layer within each of the depressions.

In an example of the fourth aspect, the causing involves introducing a cleavage agent to the flow cell.

It is to be understood that any features of this method may be combined together in any desirable manner. Moreover, it is to be understood that any combination of features of this method and/or of the flow cell may be used together, and/or combined with any of the examples disclosed herein.

Still further, it is to be understood that any features of any of the methods and/or of any of the flow cells may be combined together in any desirable manner, and/or may be combined with any of the examples disclosed herein at least to achieve the benefits as described herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

in FIG. 6B) a micrograph of the clusters generated from seeded libraries from the complex in the micro-chamber of FIG. 6A; and in FIG. 6C) a fluorescent micrograph of the real time analysis of the micro-chamber of FIG. 6B during a first base sequencing run;

FIG. 13 is a graph of the diameter of the water domain (e.g., droplet, puddle islands, liquid layer) (in µm) versus the bead density (bead/mm$^2$), where the data was extrapolated from FIGS. 12A through 12E;

FIGS. 14A and 14B depict bright-field images of flow cell surfaces prepared with fluids having the same bead concentration and different air-flow rates;

DETAILED DESCRIPTION

Figure 1:
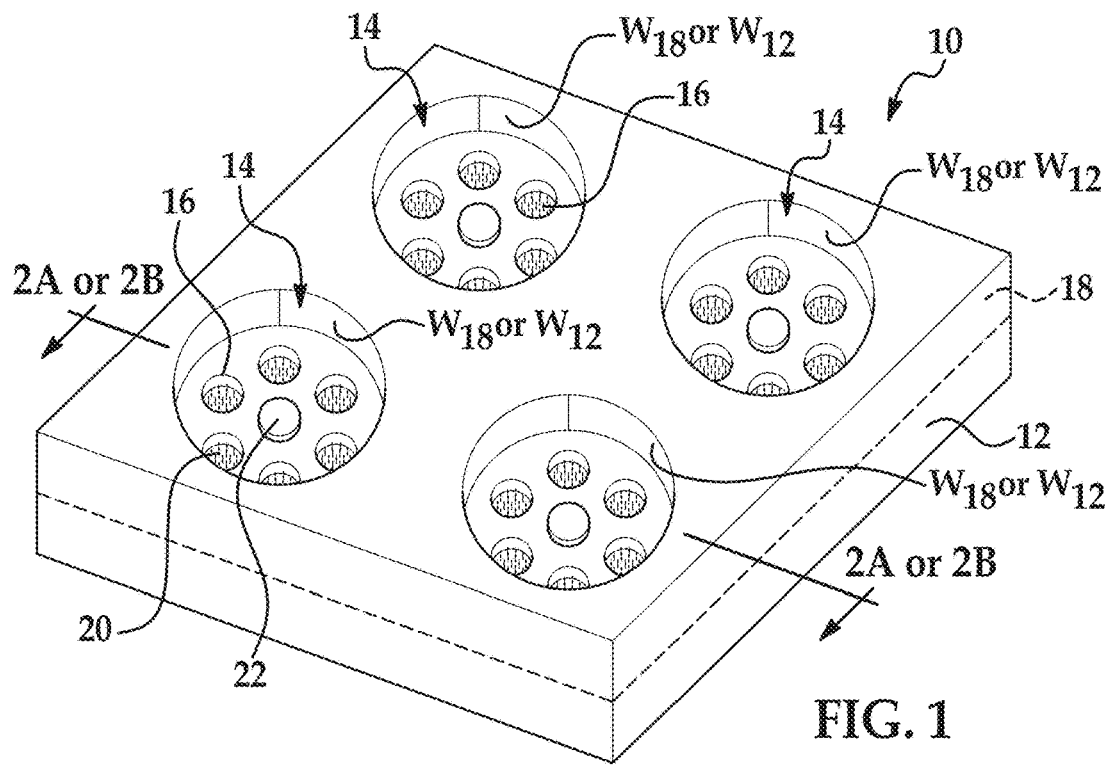
FIG. 1 is a perspective view of a portion of an example of flow cell.

The flow cells disclosed herein have a specific architecture that allows for spatial segregation of individual libraries on the flow cell. Individual libraries include similarly sized (e.g., <1000 bp) deoxyribonucleic acid (DNA) or ribonucleic (RNA) fragments of a larger nucleic acid sample, and the fragments have adapters attached at the respective ends. In some of the examples disclosed herein, the libraries are contained on or in a carrier that is introduced to the flow cell. In some other of the examples disclosed herein, the libraries are formed in situ on the flow cell after a sample is introduced to the flow cell. In some examples, the flow cell architecture includes individual capture sites that can capture individual carriers or samples. These capture sites are located in individual chambers, and thus can spatially segregate the carriers (and thus libraries within or on the carriers) or samples across the flow cell within the individual chambers. In other examples, the flow cell architecture includes chambers without capture sites. In these other examples, the chambers themselves are able to physically confine one or more of the carriers or samples.

The spatial segregation and confinement of the carrier may help to achieve spatial segregation and confinement of the library contained in or on the carrier. The spatial segregation and confinement of the sample helps to achieve spatial segregation and confinement of the library that is generated on the flow cell from the sample. In any of these examples, the library that is released from an individual carrier or formed on the flow cell from an individual sample may be contained within a particular chamber. As such, the chamber architecture reduces random binding of the library fragments across the flow cell surface. Moreover, the transport and seeding of the library fragments, as well as subsequent cluster generation, may also be confined within each chamber. As such, the confinement may result in substantially even seeding of the library fragments and thus a substantially homogenized cluster density. During sequencing, individual clusters generate "spatial clouds" of fluorescence signals as nucleotides are incorporated into respective template strands of the clusters. The confinement of the clusters into chambers can at least reduce spatial cloud cross-talk and/or overlap, and can also improve the identification of spatial clouds. Still further, because the reads obtained from any individual chamber may be generated from the same sample, they may be used to reconstruct the sample by bioinformatically stitching the short reads together.

The flow cell architectures disclosed herein can also improve the overall utilization of the surface area.

Definitions

Terms used herein will be understood to take on their ordinary meaning in the relevant art unless specified otherwise. Several terms used herein and their meanings are set forth below.

As used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, unrecited elements or method steps.

Reference throughout the specification to "one example", "another example", "an example", and so forth, means that a particular element (e.g., feature, structure, composition, configuration, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, these terms can refer to less than or equal to ±5% from a stated value, such as less than or equal to ±2% from a stated value, such as less than or equal to ±1% from a stated value, such as less than or equal to ±0.5% from a stated value, such as less than or equal to ±0.2% from a stated value, such as less than or equal to ±0.1% from a stated value, such as less than or equal to ±0.05% from a stated value.

Adapter. A linear oligonucleotide sequence that can be fused to a nucleic acid molecule, for example, by ligation or tagmentation. In some examples, the adapter is substantially non-complementary to the 3' end or the 5' end of any target sequence introduced to the flow cell. Suitable adapter lengths may range from about 10 nucleotides to about 100 nucleotides, or from about 12 nucleotides to about 60 nucleotides, or from about 15 nucleotides to about 50 nucleotides. The adapter may include any combination of nucleotides and/or nucleic acids. In some examples, the adapter includes one or more cleavable groups at one or more locations. In some examples, the adapter can include a sequence that is complementary to at least a portion of a primer, for example, a primer including a universal nucleotide sequence (such as a P5 or P7 sequence). In some examples, the adapter can include an index or barcode sequence that assists in downstream error correction, identification, or sequencing. The index may be unique to a sample or source of the nucleic acid molecule (e.g., a fragment). In some examples, the adapter can include a sequencing primer sequence or sequencing binding site. Combinations of different adapters may be incorporated into a nucleic acid molecule, such as a DNA fragment.

Capture site: A portion of a flow cell surface having been physically modified and/or modified with a chemical property that allows for localization of either a complex or a sample. In an example, the capture site may include a chemical capture agent.

Carrier. A hydrogel support that is capable of having a sequencing library contained therein or a solid support capable of having a sequencing-ready nucleic acid fragments attached to a surface thereof.

Chemical capture agent: A material, molecule or moiety that is capable of attaching, retaining, or binding to a target molecule (i.e., a complex or a sample). One example chemical capture agent includes a capture nucleic acid (e.g., a capture oligonucleotide) that is complementary to at least a portion of a target nucleic acid of or attached to the target molecule. Another example chemical capture agent is a linker. For a native DNA or RNA sample, the linker may include a nucleic acid binding moiety on one end, such as intercalators that bind via charge or hydrophobic interaction. For a cell sample, the linker may include a cell membrane binding moiety (e.g., antigens against surface proteins) or a membrane penetrating moiety (e.g., phospholipids on one end). Still another example chemical capture agent includes a member of a receptor-ligand binding pair (e.g., avidin, streptavidin, biotin, lectin, carbohydrate, nucleic acid binding protein, epitope, antibody, etc.) that is capable of binding to the target molecule (or to a linking moiety attached to the target molecule). Yet another example of the chemical capture agent is a chemical reagent capable of forming an electrostatic interaction, a hydrogen bond, or a covalent bond (e.g., thiol-disulfide exchange, click chemistry, Diels-Alder, etc.) with the target molecule.

Complex: A carrier, such as a hydrogel support or a solid support, and sequencing-ready nucleic acid fragments attached to or contained within the carrier. The carrier may also include one member of a binding pair whose other member is part of the capture site.

External immobilizing agent: A gaseous, liquid or viscous medium that is not miscible with a complex or sample that has been introduced to the flow cell chambers. The gaseous external immobilizing agent may be used to create a droplet around a complex or sample. An example of a gaseous external immobilizing agent is air that is directed at a suitable flow rate through the flow cell. For example, air may be used to aspirate a fluid containing a complex or sample from the flow cell, which forms droplets of the liquid containing the complex or sample. The formed droplet acts as a diffusion barrier. The liquid or viscous medium is used to prevent diffusion of a sequencing library released from a complex or formed within, e.g., a chamber on a flow cell surface. The external immobilizing agent can form a diffusion barrier, as the sequencing libraries or any other polynucleotide have little to no solvation in the external immobilizing agent. Example external immobilizing agents in liquid form include hydrophobic oils, such as mineral oil, silicone oil, perfluorinated oil, a fluorinated carbon oil (e.g., FLUORINERT™ FC40 from 3M), or a combination thereof. Example external immobilizing agents in viscous medium form include buffers containing polymers (e.g., polyethylene glycol, polyvinylpyrrolidone, etc.), dextran, sucrose, glycerol, and the like. In some examples, the viscous medium is a temperature responsive gel. The temperature responsive gel is non-viscous at non-seeding temperatures, and turns into a viscous medium at seeding temperatures. Examples of temperature responsive gels include poly(N-isopropylacrylamide) and polyethylene oxide-polypropylene oxide-polyethylene oxide (PEO-PPO-PEO)/laponite nanoparticle composites.

Fragment: A portion or piece of genetic material (e.g., DNA, RNA, etc.).

Hydrogel or hydrogel matrix: A colloid material including an organic polymer (natural or synthetic) that is cross-linked via covalent, ionic, or hydrogen bonds to create a three-dimensional open-lattice structure that entraps water molecules to form the gel. In an example, the hydrogel include from about 60% to about 90% fluid, such as water, and from about 10% to about 30% polymer. The hydrogel may be porous, i.e., including open/void space. The porosity is a fractional volume (dimensionless) of the hydrogel, i.e., measures void space in a material and is a fraction of the volume of voids over the total volume, as a percentage between 0 and 100% (or a fraction between 0 and 1). In an example, the porosity of the hydrogel may range from about 50% (0.5) to about 99% (0.99). The porosity may be sufficient to allow diffusion of reagents (e.g., enzymes, chemicals, and smaller sized oligonucleotides (less than 50 base pairs, e.g., primers), but prohibits diffusion of larger sized nucleic acid molecules (e.g., samples, fragments, etc.)

Hydrogel support: A hydrogel having an at least substantially spherical shape (e.g., a hydrogel bead) that can contain a sequencing library therein.

Nucleic acid molecule: A polymeric form of nucleotides of any length, and may include ribonucleotides, deoxyribonucleotides, analogs thereof, or mixtures thereof. The term may refer to single stranded or double stranded polynucleotides.

A "target" or "template" nucleic acid molecule may refer to a sequence that is to be analyzed.

The nucleotides in a nucleic acid molecule may include naturally occurring nucleic acids and functional analogs thereof. Examples of functional analogs are capable of hybridizing to a nucleic acid in a sequence specific fashion or capable of being used as a template for replication of a particular nucleotide sequence. Naturally occurring nucleotides generally have a backbone containing phosphodiester bonds. An analog structure can have an alternate backbone linkage including any of a variety known in the art. Naturally occurring nucleotides generally have a deoxyribose sugar (e.g., found in DNA) or a ribose sugar (e.g., found in RNA). An analog structure can have an alternate sugar moiety including any of a variety known in the art. Nucleotides can include native or non-native bases. A native DNS can include one or more of adenine, thymine, cytosine and/or guanine, and a native RNA can include one or more of adenine, uracil, cytosine and/or guanine. Any non-native base may be used, such as a locked nucleic acid (LNA) and a bridged nucleic acid (BNA).

Primer. A nucleic acid molecule that can hybridize to a target sequence of interest. In an example, the primer functions as a substrate onto which nucleotides can be polymerized by a polymerase. For example, an amplification primer serves as a starting point for template amplification and cluster generation. In still another example, the primer can serve as a starting point for DNA or RNA synthesis. For example, a sequencing primer can hybridize to a synthesized nucleic acid template strand in order to prime synthesis of a new strand that is complementary to the synthesized nucleic acid template strand. The primer can include any combination of nucleotides or analogs thereof. In some examples, the primer is a single-stranded oligonucleotide or polynucleotide.

Sample: Any source of genetic material, such as cells, microbiomes, or nucleic acids. In some examples, the cell is a single cell including a prokaryotic or a eukaryotic cell. In some examples, the cell is a mammalian cell, a human cell, or a bacterial cell. In some examples, the nucleic acid is a long DNA molecule, including viral nucleic acids, bacterial nucleic acids, or mammalian nucleic acids. In some examples, the sample is bound (as fragments) via insertion of transposons bound to the surface of a solid support (e.g., bead).

Sequencing-ready nucleic acid fragments: A portion (fragment) of genetic material having adapters at the 3' and 5' ends. In the sequencing-ready nucleic acid fragment, each adapter includes a known universal sequence (e.g., which is complementary to at least a portion of a primer on a flow cell) and a sequencing primer sequence. Both of the adapters may also include an index (barcode or tag) sequence. In an example, the P5 side may contain a bead index and the P7 side may contain a sample index. A sequencing-ready nucleic acid fragment may be bound via insertion, e.g., to transposons bound to the surface of a solid support (e.g., bead), or directly immobilized through a binding pair or other cleavable linker. A sequencing-ready nucleic acid fragment may also be contained within a hydrogel support.

Seeding: Immobilization of adapted fragments (e.g., sequencing-ready nucleic acid fragments) in a chamber of an example of the flow cells disclosed herein.

Sequencing library: A collection of nucleic acid fragments of one or more target nucleic acid molecules, or amplicons of the fragments. In some examples, the fragments are linked to one or more adapters at their 3' and 5' ends. In some examples, a sequencing library is prepared from one or more target nucleic acid molecules and is part of a complex. In other examples, a sequencing library is prepared on a flow cell surface using a sample.

Solid support: A small body made of a rigid or semi-rigid material having a shape characterized, for example, as a sphere, oval, microsphere, or other recognized particle shape whether having regular or irregular dimensions. The solid support can have a sequencing library attached thereto. Example materials that are useful for the solid support include, without limitation, glass; plastic, such as acrylic, polystyrene or a copolymer of styrene and another material, polypropylene, polyethylene, polybutylene, polyurethane or polytetrafluoroethylene (TEFLON® from The Chemours Co); polysaccharides or cross-linked polysaccharides such as agarose or Sepharose; nylon; nitrocellulose; resin; silica or silica-based materials including silicon and modified silicon; carbon-fiber, metal; inorganic glass; optical fiber bundle, or a variety of other polymers. Example solid supports include controlled pore glass beads, paramagnetic or other magnetic beads, thoria sol, Sepharose beads, nanocrystals and others known in the art as described, for example, in Microsphere Detection Guide from Bangs Laboratories, Fishers Ind.

Tagmentation: Modification of a nucleic acid molecule (e.g., a DNA or RNA sample) by a transposome to fragment the nucleic acid molecule and ligate adapters to the 5' and 3' ends of the fragment in a single step. Tagmentation reactions may be used to prepare sequencing libraries, in particular, complexes that include the solid support. Tagmentation reactions combine random sample fragmentation and adapter ligation into a single step, which increases the efficiency of the sequencing library preparation process.

Transposome: A complex formed between an integration enzyme (e.g., an integrase or a transposase) and a nucleic acid including an integration recognition site (e.g., a transposase recognition site).

Universal nucleotide sequence: A region of a sequence that is common to two or more nucleic acid molecules, where the molecules also have regions that differ from each other. A universal sequence that is present in different members of a collection of molecules can allow for the capture of several different nucleic acids using a population of universal capture nucleic acids (i.e., the adapter that has a sequence that is complementary to at least a portion of a primer). Similarly, a universal sequence that is present in different members of a collection of molecules can allow for the amplification or replication of several different nucleic acids using a population of universal sequencing binding sites (sequencing primer sequences).

Flow Cell Architectures

A portion of an example flow cell 10 is shown in FIG. 1. The flow cell 10 includes a substrate 12, a plurality of chambers 14 defined on or in the substrate 12, a plurality of depressions 16 defined in the substrate 12 and within a perimeter of each of the plurality of chambers 14, primers 20 attached within each of the depressions 16, and a capture site 22 located within each of the plurality of chambers 14.

The substrate 12 is generally rigid and is insoluble in an aqueous liquid. The substrate 12 may be a single layered or a multi-layered structure. Examples of suitable substrates 12 include epoxy siloxane, polyhedral oligomeric silsequioxanes (POSS) or derivatives thereof, glass, modified glass, plastics, nylon, ceramics/ceramic oxides, silica (silicon oxide ($SiO_2$)), fused silica, silica-based materials, aluminum silicate, silicon, modified silicon (e.g., boron doped p+ silicon), silicon nitride ($Si_3N_4$), tantalum pentoxide ($TaO_5$) or other tantalum oxide(s) ($TaO_x$), hafnium oxide ($HaO_2$), inorganic glasses, or the like. Some examples of suitable plastics for the substrate 12 include acrylics, polystyrene, copolymers of styrene and other materials, polypropylene, polyethylene, polybutylene, polyurethanes, polytetrafluoroethylene (such as TEFLON® from The Chemours Co.), cyclic olefins/cyclo-olefin polymers (COP) (such as ZEONOR® from Zeon), polyimides, etc. The substrate 12 may also be glass or silicon or POSS, with a coating layer of tantalum oxide or another ceramic oxide at the surface. The substrate 12 may also be glass or silicon, with a coating layer of POSS at the surface. Another example of a suitable substrate 12 is a silicon-on-insulator substrate.

The form of the substrate 12 may be a wafer, a panel, a rectangular sheet, a die, or any other suitable configuration. In an example, the substrate 12 may be a circular wafer or panel having a diameter ranging from about 2 mm to about 300 mm. As a more specific example, the substrate 12 is a wafer having a diameter ranging from about 200 mm to about 300 mm. In another example, the substrate 12 may be a rectangular sheet or panel having its largest dimension up to about 10 feet (~3 meters). As a specific example, the substrate 12 is a die having a width ranging from about 0.1 mm to about 10 mm. While example dimensions have been provided, it is to be understood that a substrate 12 with any suitable dimensions may be used.

The plurality of chambers 14 may be defined on or in the substrate 12.

Figure 2A:
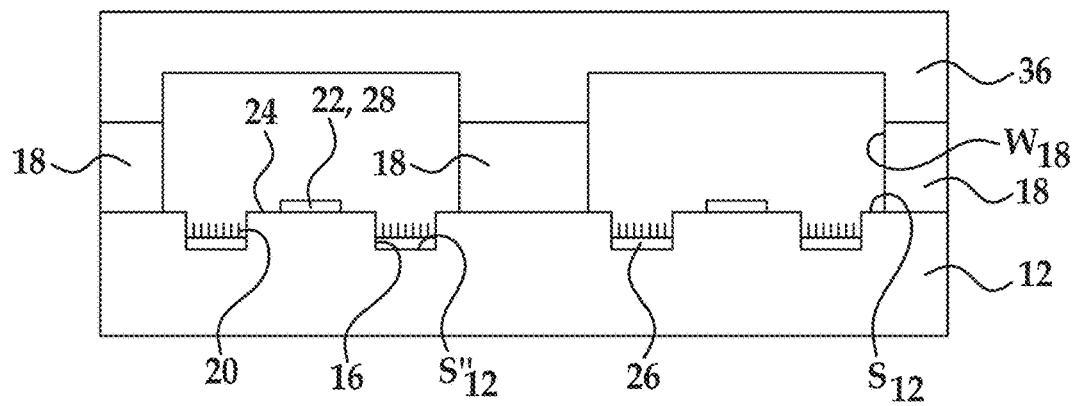
FIGS. 2A and 2B are cross-sectional views taken along lines 2A-2A and 2B-2B, respectively, of FIG. 1, that illustrate different examples of the chamber architecture of the flow cell.

An example of the chambers 14 defined on the substrate 12 is shown in FIG. 2A. In the examples disclosed herein, the chamber 14 is considered to be "defined on" the substrate 12 when i) the substrate surface $S_{12}$ defines a bottom surface of the chamber 14 and ii) a separate material 18 is positioned on the substrate 12 and defines the walls $W_{18}$ of the chamber 14. When a silicon-on-insulator substrate is used with the separate material 18, the walls $W_{18}$ of the chamber 14 may be partially defined by the outermost silicon layer of the substrate and the separate material 18.

The separate material 18 may be a hydrophobic material, such as a fluorinated polymer, a perfluorinated polymer, a silicon polymer, or a mixture thereof. The polymer backbone of the hydrophobic material may be carbon or silicon, or a combination thereof. In some examples, the fluorinated polymer is an amorphous fluoropolymer (commercially available examples of which include those in the CYTOP® series from AGC Chemicals, which have one of the following terminal functional groups: A type: —COOH, M type: —CONH—Si(OR)$_n$ or S type: —CF$_3$), a polytetrafluoroethylene (such as TEFLON®, from The Chemours Co.), parylen (e.g., grades A, F, HT), a fluorinated hydrocarbon, a fluoroacrylic copolymer (such as FLUOROPEL™, from Cytonix), (tridecafluoro-1,1,2,2-tetrahydrooctyl)trichlorosilane (FOTS), a fluorosilane, or a plasma-deposited fluorocarbon, or a mixture thereof. As another example, the hydrophobic polymer or hydrophobic polymer layer may include a hydrophobic hydrocarbon, such as 1-heptadecyne. In some examples, the silicon polymer is polydimethylsiloxane or another siloxane. It may be particularly desirable to utilize a hydrophobic material for the separate material 18 when the material(s) in the depressions 16 is/are hydrophilic. Other polymers may be used as the separate material 18, as long as the resulting structure is able to induce pearling of a liquid moving across the structure. Alternatively, if the material(s) in the depressions 16 is/are hydrophobic, it may be desirable to utilize a hydrophilic material for the separate material 18. The hydrophobic or hydrophilic characteristics of the separate material 18 may help to guide reagents toward the depressions 16.

In one example, the separate material 18 may be deposited on the substrate 12 and then patterned using photolithography. In examples where the substrate 12 is the silicon-on-insulator substrate, the separate material 18 and the outermost silicon layer may be patterned using photolithography. As an example, a mask (e.g., a photoresist) may be used to define the space/location where the separate material 18 will be deposited. The separate material 18 may then be deposited, and the mask removed (e.g., via lift-off, dissolution, or another suitable technique). As another example, the separate material 18 may be deposited and then the mask may be deposited on the separate material 18. The mask may be patterned using photolithography, and any exposed portions of the separate material 18 may be removed via plasma etching or dry etching with oxygen gas. The mask may then be removed to reveal the remaining separate material 18. In still another example, the separate material 18 may be laminated to the substrate 12 or transferred from a mold or a sacrificial layer to the substrate 12. In still another example, the separate material 18 may be printed using microcontact printing (using a stamp), aerosol printing, or inkjet printing.

Figure 2B:
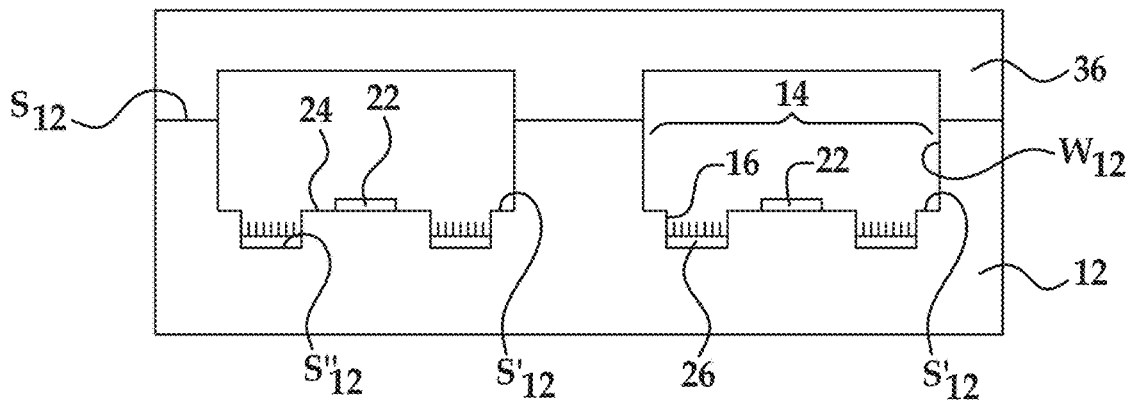

An example of the chambers 14 defined in the substrate 12 is shown in FIG. 2B. In the examples disclosed herein, the chamber 14 is considered to be "defined in" the substrate 12 when i) the substrate surface $S_{12}$ defines interstitial regions around the chamber 14, ii) another substrate surface $S'_{12}$ defines a bottom surface of the chamber 14, and iii) the substrate 12 also defines the walls $W_{12}$ of the chamber 14.

In this example, the chambers 14 may be patterned into the substrate. Patterning may involve etching the chambers 14 into the substrate 12 and/or using imprint lithography.

Whether formed on or in the substrate 12, the chambers 14 may be distributed across the substrate 12 in any suitable pattern or layout. Many different layouts of the chambers 14 may be envisaged, including regular, repeating, and non-regular patterns. In an example, the chambers 14 are disposed in a hexagonal grid for close packing and improved density. Other layouts may include, for example, parallelogram layouts (i.e., rectangular, square, etc.), triangular layouts, circular layouts, and so forth. In some examples, the layout or pattern can be an x-y format of the chambers 14 that are in rows and columns (as shown in FIG. 1).

The chamber 14 may have any suitable shape, such as a circle (as shown in FIG. 1), an oval, a polygon (e.g., triangle, quadrilateral, pentagon, etc.), etc.

The size of each chamber 14 may be characterized by its opening area, diameter, and/or length and width. As shown in FIG. 1, the flow cell 10 has a plurality of depressions 16 located within each of the chambers 14. As such, the size of the chamber 14 is larger than the size of each depression 16. In other words, the dimension(s) of the chamber 14 is/are larger than the dimension(s) of each depression 16. In this example, "dimension" refers to the area occupied by each chamber opening or depression opening, and/or the diameter of the chamber 14 or depression 16, and/or the length and width of each chamber 14 or depression 16. In the example shown in FIG. 1, the opening area and the diameter of each of the chambers 14 is larger than the opening area and the diameter of each of the depressions 16. The opening area, and the diameter or length and width of each chamber 14 depends upon the number of depressions 16 that are is to be located within the chamber 14, and the size of the capture site 22 that is to be located within the chamber 14.

Figure 4A:
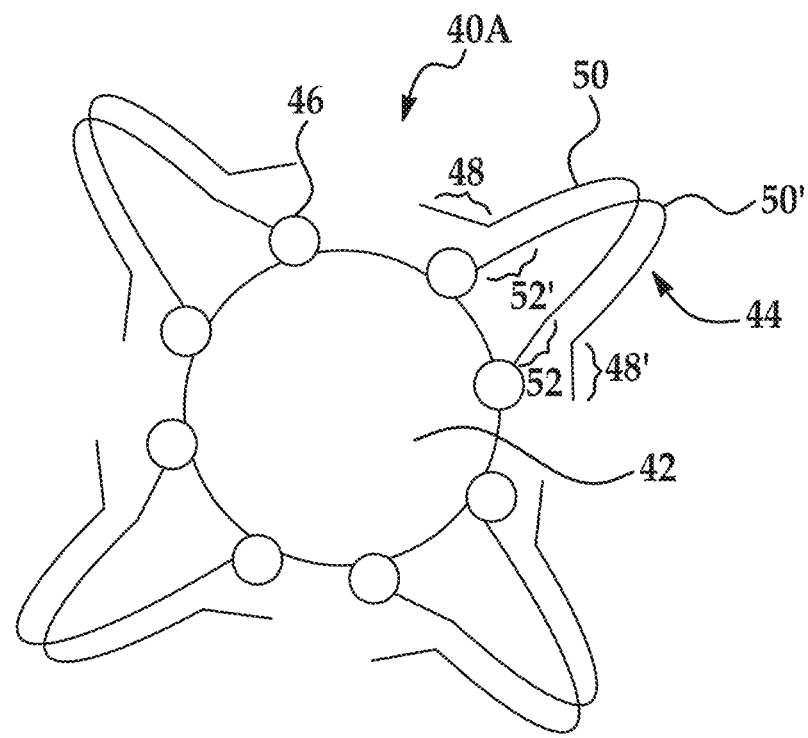
FIGS. 4A through 4C are schematic illustrations of different examples of the complexes disclosed herein.
Figure 4B:
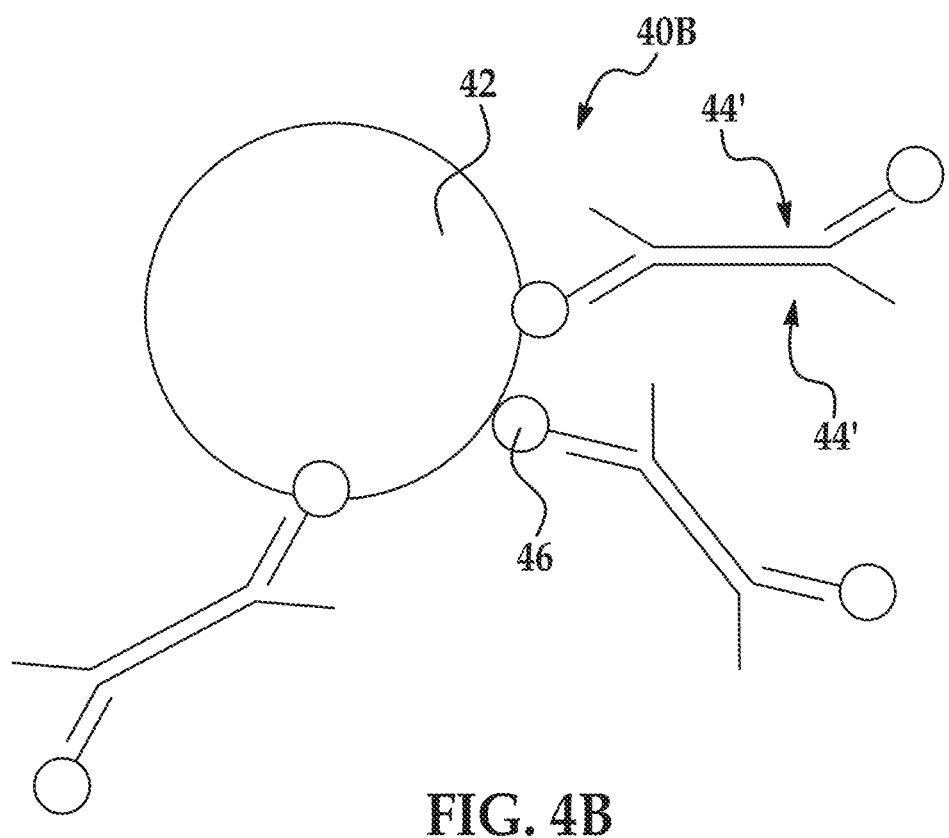
Figure 4C:
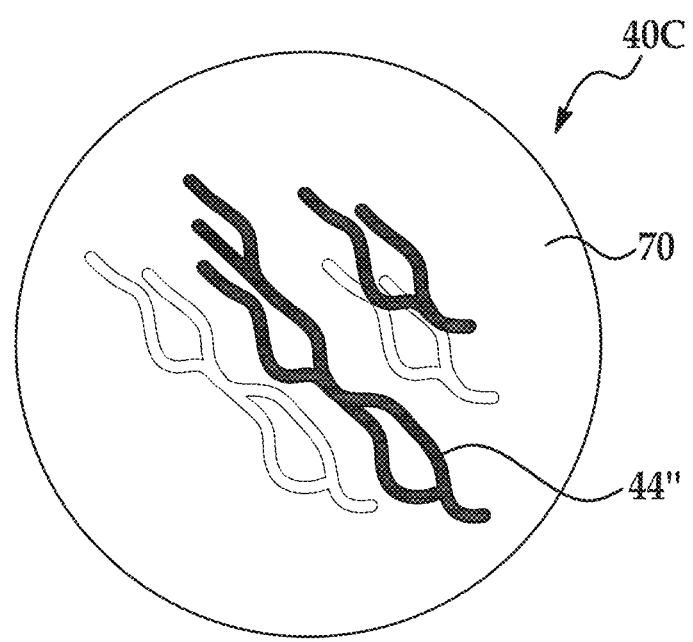

The area occupied by each chamber opening can be selected so that a complex (examples of which are shown in FIGS. 4A-4C) can enter the chamber 14 and attach to the capture site 22 in the chamber 14. In an example, the area for each chamber opening can be at least about 1 $\mu m^2$, at least about 10 $\mu m^2$, at least about 100 $\mu m^2$, or more. The area occupied by each chamber opening can be greater than or between the values specified above.

In some instances, the diameter or length and width of each chamber 14 can be at least about 1 $\mu m$, at least about 10 $\mu m$, at least about 20 $\mu m$, at least about 30 $\mu m$, at least about 40 $\mu m$, at least about 50 $\mu m$, at least about 100 $\mu m$, or more. An example of the chamber diameter ranges from about 1 $\mu m$ to about 1000 $\mu m$. Another example of the chamber diameter ranges from about 10 $\mu m$ to about 50 $\mu m$. When the chamber 14 has a length and width, it is to be understood that the length and width may be the same or different.

The chamber 14 may also have a depth that depends upon the technique used to form the chamber 14. For example, the depth of each chamber 14 can be a monolayer thick when microcontact, aerosol, or inkjet printing is used to form the chamber walls $W_{18}$. For other examples, the depth of each chamber 14 can be about 1 $\mu m$, about 10 $\mu m$, about 50 $\mu m$, or more. In another example, the depth is at least about 50% of an average diameter of a complex that is to be introduced into the chamber 14. In an example, this depth may range from about 10 $\mu m$ to about 30 $\mu m$. This depth is sufficient to block lateral diffusion of released library fragments between adjacent chambers 14, thus maintaining the released library fragments within the chamber 14 without any external immobilization agent. In another example, the depth is 5 $\mu m$ or less. It is to be understood that the depth of each chamber 14 can be greater than, less than or between the values specified above.

Adjacent chambers 14 may be separated by the surface $S_{18}$ of the additional material 18 (shown in FIG. 2A) or by the surface $S_{12}$ of the substrate 12 (shown in FIG. 2B). The average chamber pitch represents the spacing from the center of one chamber 14 to the center of an adjacent chamber 14 (center-to-center spacing) or from the edge of one chamber 14 to the edge of an adjacent chamber 14 (edge-to-edge spacing). The layout or pattern of the chambers 14 can be regular, such that the coefficient of variation around the average pitch is small, or the layout or pattern can be non-regular in which case the coefficient of variation can be relatively large. In either case, the average pitch can be, for example, at least about 1 $\mu m$, at least about 5 $\mu m$, at least about 10 $\mu m$, at least about 100 $\mu m$, or more. In one example, the average pitch is 2 times the diameter of the chamber 14. The average pitch for a particular pattern of chambers 14 can be between one of the lower values and one of the upper values selected from the ranges above. While example average chamber pitch values have been provided, it is to be understood that other average chamber pitch values may be used.

The plurality of depressions 16 may be defined in the substrate 12. In the examples disclosed herein, the depressions 16 are considered to be "defined in" the substrate 12 when i) the substrate surface $S_{12}$ or $S'_{12}$ defines interstitial regions 24 that separate the depressions 16, ii) another substrate surface $S''_{12}$ defines a bottom surface of the depressions 16, and iii) the substrate 12 also defines the walls of the depressions 16.

The depressions 16 may be patterned into the substrate 12. Patterning may involve etching the depressions 16 into the substrate 12 and/or using imprint lithography.

Respective sub-sets of the depressions 16 may be distributed across each of the chamber 14 in any suitable pattern or layout. The pattern of depressions 16 in each chamber 14 may be the same, or different patterns of depressions 16 may be used in different chambers 14. Many different patterns/ layouts of the depressions 16 may be envisaged, including regular, repeating, and non-regular patterns. In an example, the depressions 16 are disposed in a hexagonal grid for close packing and improved density. Other layouts may include, for example, parallelogram layouts (i.e., rectangular, square, etc.), triangular layouts, circular layouts, and so forth. In the example shown in FIG. 1, the depressions 16 in each chamber 14 are arranged in a circular pattern around the capture site 22. As shown in FIG. 1, the plurality of chambers 14 may be arranged in a first pattern (e.g., 2×2) across the substrate 12, and respective sub-sets of depressions are arranged in a second pattern (e.g., circular) within each of the chambers 14.

Each depression 16 may have any suitable shape (and corresponding 3-dimensional geometry), such as a circle (as shown in FIG. 1), an oval, a polygon (e.g., triangle, quadrilateral, pentagon, etc.), etc.

The size of each depression 16 may be characterized by its opening area, diameter, and/or length and width. As shown in FIG. 1, the flow cell 10 has a plurality of depressions 16 located within each of the chambers 14. As such, the size of each depression 16 is smaller than the size of the chamber 14 in which it is located.

The area occupied by each depression opening can be selected so that a complex cannot enter the depression 16. In an example, the area for each depression opening can be at least about $1 \times 10^{-4}$ µm², at least $1 \times 10^{-3}$ µm², at least about $1 \times 10^{-2}$ µm², at least about 0.1 µm², at least about 0.5 µm², at least about 1 µm², or at least about 4 µm². The area occupied by each depression opening can be less than or between the values specified above.

In some instances, the diameter or length and width of each depression 16 can be at least about 1 nm, at least about 50 nm, at least about 100 nm, at least about 500 nm, or more, as long as the dimension is less than the chamber diameter or length and width. An example of the depression diameter ranges from about 1 nm to about 500 nm. Another example of the depression diameter ranges from about 300 nm to about 2 µm.

The depressions 16 may also have a depth. As examples, the depth of each depression 16 can be at least about 10 nm, at least about 50 nm, at least about 1 µm, up to about 2 µm. In some examples, the depth is about 0.4 µm. It is to be understood that the depth of each depression 16 can be greater than, less than or between the values specified above.

In an example, the aspect ratio (diameter:depth) of the depressions 16 may range from about 1:1 to about 1:2, or from about 1:1.25 to about 1:1.75.

Adjacent depressions 16 may be separated by the interstitial regions 24 within a given chamber 14. The average depression pitch represents the spacing from the center of one depression 16 to the center of an adjacent depression 16 (center-to-center spacing) or from the edge of one depression 16 to the edge of an adjacent depression 16 (edge-to-edge spacing). The layout or pattern of the depressions 16 can be regular, such that the coefficient of variation around the average pitch is small, or the layout or pattern can be non-regular in which case the coefficient of variation can be relatively large. In either case, the average pitch can be, for example, at least about 10 nm, at least about 0.1 µm, at least about 0.5 µm, or more, depending upon the dimensions of the chamber 14. Alternatively or additionally, the average pitch can be, for example, at most about 0.5 µm, or at most about 0.1 µm, or less. The average pitch for a particular pattern of depressions 16 can be between one of the lower values and one of the upper values selected from the ranges above.

Primers 20 are also attached within each of the depressions 16. The primers 20 may be any forward amplification primer or reverse amplification primer that includes a functional group that can attach to a layer 26 that is present at least at the bottom of each depression 16 (i.e., on surface $S''_{12}$). The primers 20 may form a lawn, within each depression 16, of capture oligonucleotides that can bind to adapters of the sequencing-ready nucleic acid fragments.

In an example, the primers 20 can be immobilized to the layer 26 by single point covalent attachment at or near the 5' end of the primers 20. This attachment leaves i) the adapter-specific portion of the primers 20 free to anneal to its cognate sequencing-ready nucleic acid fragment and ii) the 3' hydroxyl group free for primer extension. Any suitable covalent attachment may be used for this purpose. Examples of terminated primers that may be used include an alkyne terminated primer, a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, a phosphoramidite terminated primer, and a triazolinedione terminated primer. In another example, the primers 20 can be immobilized to the layer 26 through a non-covalent interaction. In an example, each primer 20 may include a linking molecule (e.g., biotin) that can non-covalently bind to the layer 26. In some examples, two different primers 20 are used. Specific examples of suitable primers 20 include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms.

In an example, the layer 26 is a substance that is capable of non-covalently binding to a linking molecule that is attached to the primer 20. As one example, the linking molecule is biotin, and the layer 26 is avidin, streptavidin, etc. In this example, the layer 26 may by applied by microcontact printing or aerosol printing, deposition and polishing, or another suitable selective deposition technique.

In another example, the layer 26 is a polymer that is capable of covalently attaching to the primer 20. The bottom surface (e.g., $S''_{12}$) of the depressions 16 may be activated, and then the polymer may be applied to form the layer 26.

In some examples, activation may involve applying a silane or silane derivative (e.g., norbornene silane). In other examples, activation may involve plasma ashing to generate surface-activating agent(s) (e.g., –OH groups) that can adhere to the polymer used to form the layer 26.

An example of the polymer that may be used to form the layer 26 includes an acrylamide copolymer, such as poly (N-(5-azidoacetamidylpentyl)acrylamide-co-acrylamide, PAZAM. PAZAM and some other forms of the acrylamide copolymer are represented by the following structure (I):

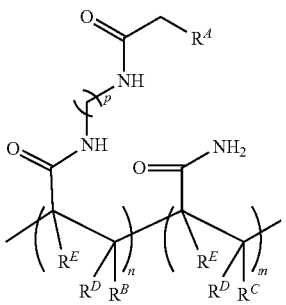

wherein:

$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;

$R^B$ is H or optionally substituted alkyl;

$R^C$, $R^D$, and $R^E$ are each independently selected from the group consisting of H and optionally substituted alkyl;

each of the $-(CH_2)_p-$ can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

In some examples, PAZAM is a linear polymer. In some other examples, PAZAM is a lightly cross-linked polymer.

In other examples, the polymer that may be used to form the layer 26 may be a variation of the structure (I). In one example, the acrylamide unit may be replaced with N,N-dimethylacrylamide

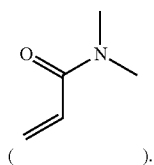

In this example, the acrylamide unit in structure (I) may be replaced with

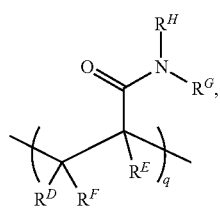

where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

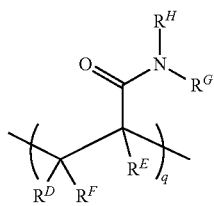

in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

It is to be understood that other polymers or molecules may be used to form the layer 26, as long as they are functionalized to interact with the surface S"$_{12}$ and the subsequently applied primers 20. Other examples of suitable polymers for the layer 26 include those polymers having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymers for the layer 26 include mixed copolymers of acrylamides and acrylates.

The method(s) used to functionalize the depressions 16 with the polymer that forms the layer 26 may depend upon whether the chambers 14 are defined on or in the substrate 12.

For example, when the chambers 14 are defined on the substrate 12 by the separate material 18, it is to be understood that the substrate surfaces S$_{12}$ and S"$_{12}$ may be treated to functionalize the depressions 16, and then the separate material 18 may be attached to the surface S$_{12}$ to define the chambers 14. In one example, the silane or silane derivative may be deposited on the substrate surfaces S$_{12}$ and S"$_{12}$ using vapor deposition, spin coating, or other deposition methods. In another example, the substrate surfaces S$_{12}$ and S"$_{12}$ may be exposed to plasma ashing. The polymer (that will form the layer 26) may then be applied to the activated substrate surfaces S$_{12}$ and S"$_{12}$ using spin coating, or dipping or dip coating, or flow of the material under positive or negative pressure, or another suitable technique. In one example, the polymer may be present in a mixture (e.g., with water or with ethanol and water). Depending upon the polymer, the applied mixture may be exposed to a curing process to form the (covalently bonded) layer 26 across the surfaces S$_{12}$ and S"$_{12}$. In an example, curing may take place at a temperature ranging from room temperature (e.g., about 25° C.) to about 95° C. for a time ranging from about 1 millisecond to about several days. Polishing may then be performed in order to remove the layer 26 from the surface S$_{12}$, while leaving the layer 26 on the surface S"$_{12}$ at least substantially intact. In these examples, the separate material 18 may then be formed on the surface S$_{12}$ as described herein (e.g., photolithography, printing, film transfer or lamination, etc.).

For another example, when the chambers 14 are defined in the substrate 12, it is to be understood that selective deposition techniques may be used to functionalize the depressions 16. In this example, the silane or silane derivative and then the polymer mixture may be deposited by microcontact printing, aerosol printing, or inkjet printing.

A grafting process may be performed to graft the primers 20 to the layer 26 in the depressions 16. In an example, grafting may involve flow through deposition (e.g., using a temporarily bound lid), dunk coating, spray coating, puddle dispensing, or by another suitable method that will attach the primer(s) 20 to the layer 26 in the depressions 16. Each of these example techniques may utilize a primer solution or mixture, which may include the primer(s), water, a buffer, and a catalyst. With any of the grafting methods, the primers 20 react with reactive groups of the polymer layer 26 in the depressions 16 and have no affinity for the interstitial regions 24, the other substrate surfaces $S_{12}$ or $S'_{12}$, or the separate material 18. As such, the primers 20 selectively graft to the polymer layer 26 in the depressions 16.

Figure 3A:
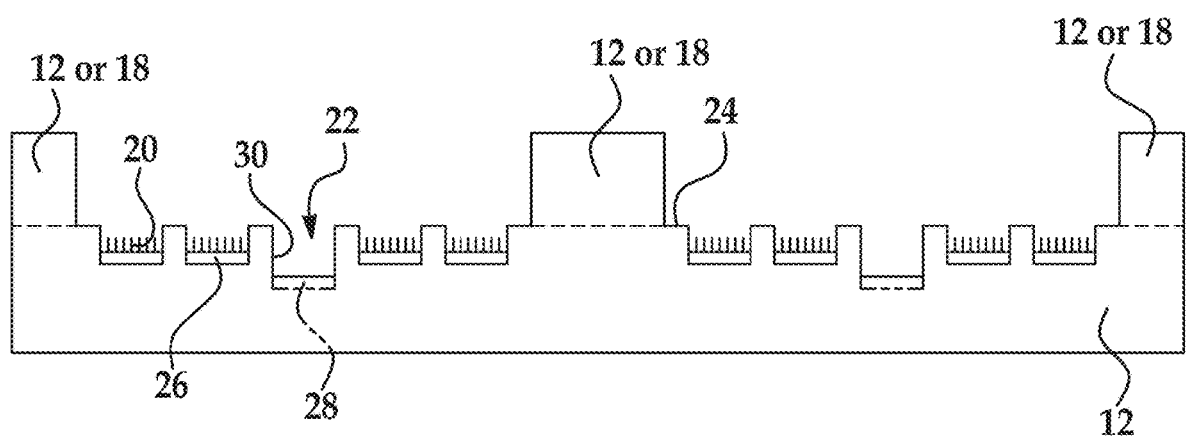
FIGS. 3A through 3C are cross-sectional views illustrating different examples of capture sites that may be used in the flow cell.
Figure 3B:
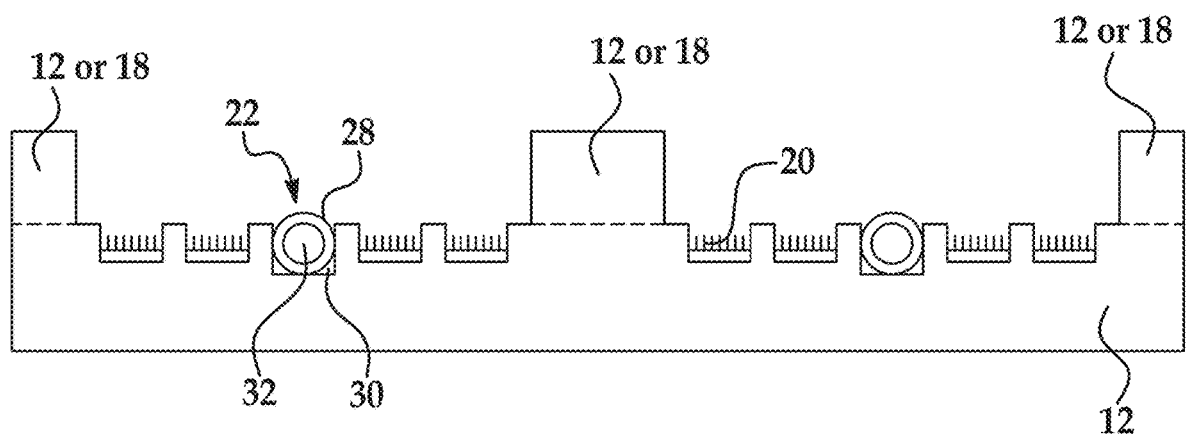
Figure 3C:
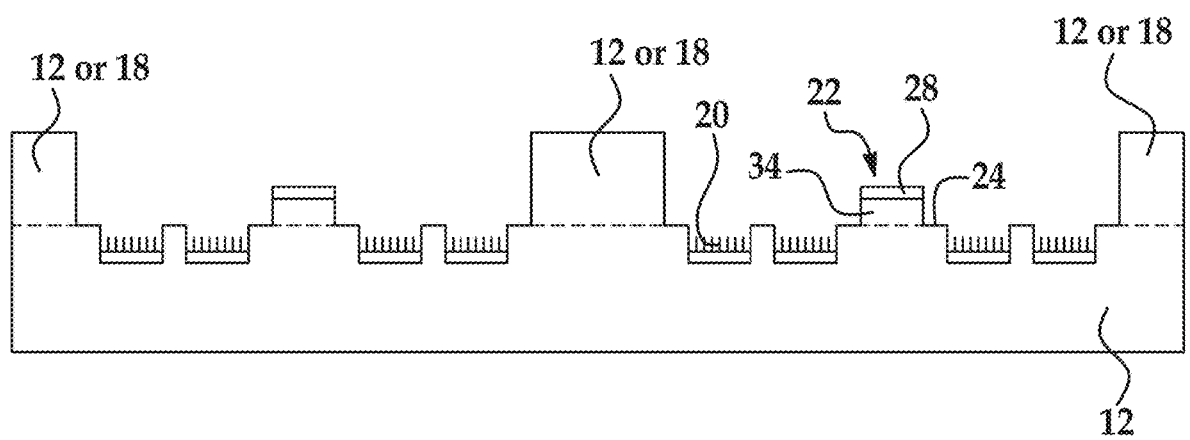

Examples of the flow cells 10 disclosed herein include a capture site 22 located within each of the plurality of chambers 14. One example of the capture site 22 is shown in FIGS. 1, 2A and 2B, and other examples of the capture site 22 are shown in FIGS. 3A through 3C.

The capture site 22 is physically and/or chemically capable of immobilizing a complex or a sample within a particular chamber 16. Physical immobilization may be possible with the example shown in FIG. 3A. Chemical immobilization involves the chemical capture agent 28 defined herein. When the capture site 22 is capable of chemical immobilization, the chemical capture agent 28 used may depend, in part, upon the complex or sample that is to be introduced into the flow cell 10.

In some of the examples disclosed herein, the capture site 22 is capable of capturing a complex that is introduced into the flow cell 10. In other examples disclosed herein, the capture site 22 is capable of capturing a sample that is then subjected to further processing on the flow cell surface to generate a library.

In FIGS. 1, 2A and 2B, the capture site 22 is formed at the center of the chamber 14. It is to be understood that the capture site 22 may be positioned at any desirable position within the chamber 14, which may depend upon the arrangement of the depressions 16. The position of the capture sites 22 across the substrate 12 may be uniform (e.g., each capture site 22 is in substantially the same position (e.g., center, far left, etc.) within each chamber 14) or may be non-uniform (e.g., the captures sites 22 are in different positions within the different chambers 24).

The capture site 22 may have any suitable shape, geometry and dimensions, which may depend, at least in part, on the configuration of the capture site 22 (e.g., a patch, a well, a protrusion, etc.), the dimensions of the chamber 14 in which the capture site 22 is formed, and the type of complex or sample that is to be captured by the capture site 22.

In the example shown in FIGS. 1, 2A and 2B, the capture site 22 is a chemical capture agent 28 that is applied on a portion of the interstitial regions 24. Any examples of the chemical capture agent 28 disclosed herein may be used. In one example, the chemical capture agent 28 may be deposited in a desirable location using microcontact printing, aerosol printing, etc. In another example, a mask (e.g., a photoresist) may be used to define the space/location where the chemical capture agent 28 will be deposited. The chemical capture agent 28 may then be deposited, and the mask removed (e.g., via lift-off, dissolution, or another suitable technique). In this example, the chemical capture agent 28 may form a monolayer or thin layer of the chemical capture agent 28, which may be referred to as a patch.

Other examples of the captures site 22 are shown in FIGS. 3A, 3B and 3C. It is to be understood that any of the capture sites 22 may be used in any example of the flow cell 10, including those with the chamber 14 defined on the substrate 12 (and including the additional material 18) or those with the chamber 14 defined in the substrate 12.

In FIG. 3A and FIG. 3B, the capture site 22 includes a well 30 that is defined in the substrate 12. The well may be "defined in" the substrate 12 in the same manner as the depressions 16. The wells 30 may be formed using etching, photolithography, and/or imprinting depending upon the substrate 12 that is used. In an example, the wells 30 may be formed at the same time as the depressions 16.

The wells 30 may have any suitable shape and geometry, including any of those described herein for the depressions 16.

In the example shown in FIG. 3A, the well 30 has an opening dimension that is larger than an opening dimension of each of the plurality of depressions 16. In this example, the "opening dimension" refers to the area occupied by each well opening and each depression opening, and/or the diameter of each well opening and each depression opening and/or the length and width of each well opening and each depression opening. The opening dimension of the well 30 may depend upon the size of the complex or sample to be introduced thereto. In the example shown in FIG. 3A, the depressions 16 are smaller than the well 30, in part so that they physically cannot accommodate the complex or sample. In FIG. 3A, the depth of the depressions 16 is less than the depth of the well 30, although it is to be understood that the diameter or length and width may also be smaller. In other examples, the well 30 may be similar in size to or the same size as the depressions 16. In one example, the chemical capture agent 28 includes the primers 20, and thus any of the depressions 16 may function as the well 30 to capture the complex or sample.

In some examples, the wells 30 do not have an additional chemical capture agent 28 added thereto. In these examples, the opening dimensions enable the complexes or samples to self-assemble into the wells 30 and not the depressions 16 by size exclusion.

In other examples, the wells 30 do have an additional chemical capture agent 28 added thereto (as shown in phantom in FIG. 3A). Any examples of the chemical capture agent 28 disclosed herein may be used. In one example, the chemical capture agent 28 may be deposited in the wells 30 using microcontact printing. In another example, a mask (e.g., a photoresist) may be used to deposit the chemical capture agent 28 in the wells 30. In these examples, the opening dimensions enable the complexes or samples to self-assemble into the wells 30 and not the depressions 16 by size exclusion and by the binding affinity between the chemical capture agent 28 and the complex or sample introduced into the flow cell 10.

The capture site 22 in FIG. 3B includes the well 30 and a capture bead 32 having a chemical capture agent 28 on a surface thereof. The capture bead 32 may be sized to fit into the wells 30 and not into the depressions 16. In some examples, the capture bead 32 may be co-planar with or extend slightly above the adjacent interstitial regions 24 so that the complex or sample that ultimately attaches thereto is not confined within the well 30. In an example, the capture bead 32 is selected from the group consisting of silicon dioxide, a superparamagnetic material, polystyrene, and an acrylate. Any examples of the chemical capture agent 28 disclosed herein may be used on the surface of the capture bead 32, and may be coated on the capture bead 32 before it is introduced into the well 30.

The depth of the well 30 (in FIG. 3A or 3B) may vary depending upon whether the chemical capture agent 28 is introduced thereto and whether the capture bead 32 is introduced thereto. The depth may be selected at least to accommodate these materials (i.e., the material is contained within the well 30). In an example, the depth of the well 30 ranges from about 1 nm to about 5 µm. In other examples, the depth of the well 30 range from about 1 nm to about 100 nm, or from about 1 µm to about 5 µm. Other depths are also possible.

In FIG. 3C, the capture site 22 includes a protrusion 34 that is defined in the substrate 12 or on the surface $S_{12}$ of the substrate 12. The protrusion 34 is a three-dimensional structure that extends outward (upward) from an adjacent surface. When the protrusion 34 is formed in the substrate 12, the substrate 12 is patterned (e.g., via etching, photolithography, imprinting, etc.,) so that it extends above the adjacent surrounding interstitial regions 24. When the protrusion 34 is formed on the substrate 12, the additional material 18 is patterned (e.g., via etching, photolithography, imprinting, etc.,) so that it extends above the adjacent surrounding substrate surface $S_{12}$.

While any suitable three-dimensional geometry may be used for the protrusion 34, a geometry with an at least substantially flat top surface may be desirable. Example protrusion geometries include a sphere, a cylinder, a cube, polygonal prisms (e.g., rectangular prisms, hexagonal prisms, etc.), or the like.

As shown in FIG. 3C, a chemical capture agent 28 is applied on the top surface of the protrusion 34. Any examples of the chemical capture agent 28 disclosed herein may be used, and any deposition technique may be used to apply the chemical capture agent 28 to the top surface of the protrusion 34.

In some instances, it may be desirable to have one capture site 22 per chamber 14. In other instances, it may be desirable to have multiple isolated captures sites 22 per chamber 14. The number of capture sites 22 in an individual chamber 14 may help to control the number of complexes that become captured within a given chamber 14.

Referring back to FIGS. 2A and 2B, the flow cell 10 may also include a lid 36 bonded to the separate material 18 or to the substrate 12. The lid 36 may be positioned so that it defines a single flow channel (in fluid communication with the plurality of chambers 14) or multiple, fluidically separated flow channels (each of which is in fluid communication with a sub-set of the plurality of chambers 14).

The lid 36 may be any material that is transparent to an excitation light that is directed toward the depression(s) 16. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid 36 may be bonded using any suitable technique, such as laser bonding, diffusion bonding, anodic bonding, eutectic bonding, plasma activation bonding, glass frit bonding, or others methods known in the art. In an example, a spacer layer may be used to bond the lid 36 to the portion of the separate material 18 or of the substrate 12. The spacer layer may be any material that will seal at least some of the separate material 18 or the substrate 12 and the lid 36 together.

While not shown, it is to be understood that one or more additional layers may be incorporated between the substrate 12 and the lid 36 or between the substrate 12 and the depressions 16. These additional layer(s) may be selected to function as a planar waveguide for the excitation of the depressions 16 with an evanescent field.

Figure 5:
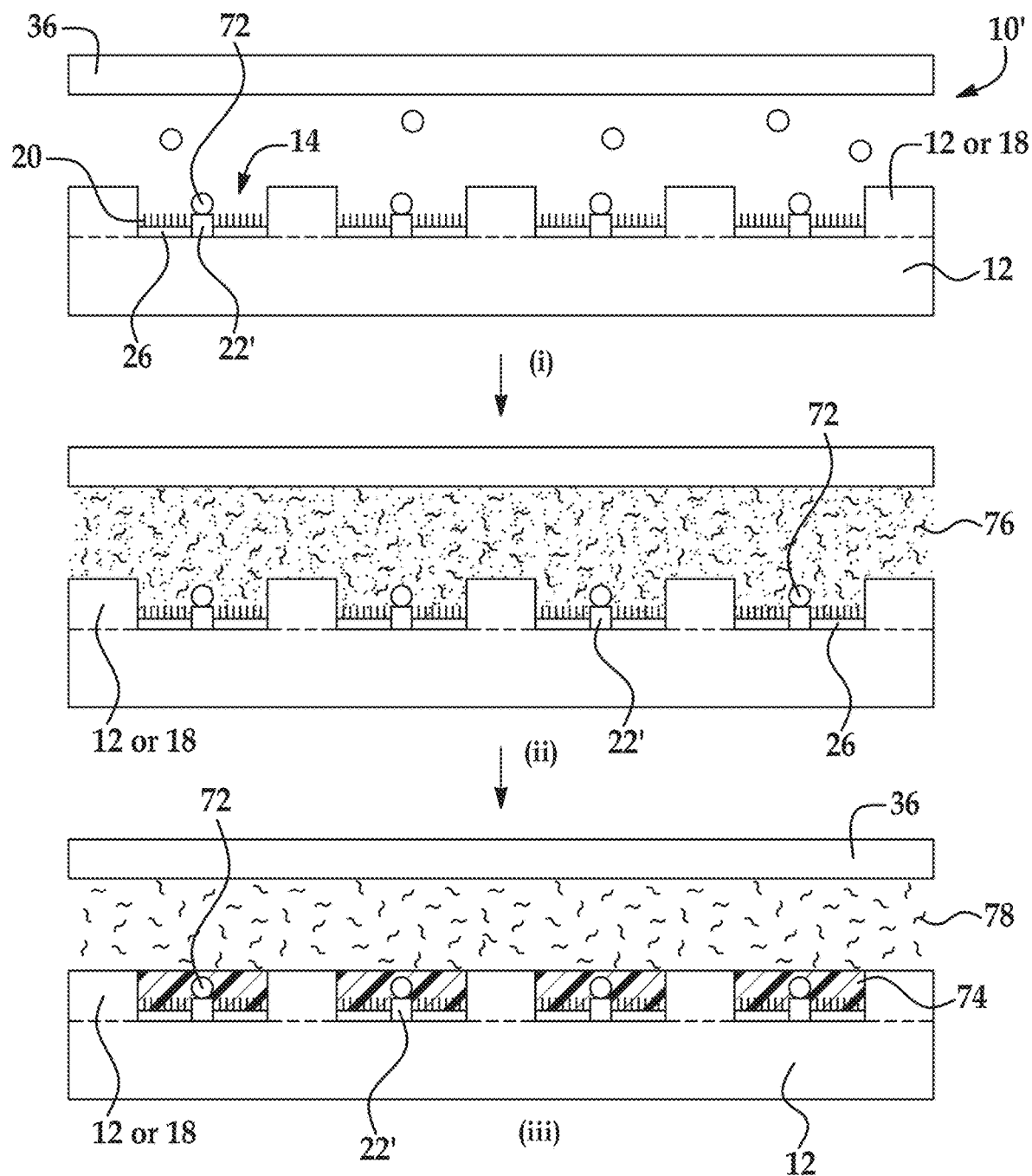
FIG. 5 is a schematic flow diagram including (i) through (iii), illustrating an example of a method wherein a hydrogel matrix is formed within the chambers of a flow cell.

It is to be understood that other flow cell architectures are also contemplated herein. As one example, the flow cell 10 may include chambers 14 and capture sites 22, but no depressions 16. In these examples, the primers 20 may be attached to a bottom surface of the chamber 14 rather than in discrete depressions 16. The bottom surface of the chamber 14 may be functionalized with the layer 26 and the primers 20. In some examples, the layer 26 may be applied to the entire bottom surface (except where the capture site 22 is formed). In these examples, an at least substantially uniform primer 20 lawn may be formed across the bottom surface of the chamber 14. In other examples, the layer 26 may be applied as islands (e.g., circular, triangular, rectangular, etc. in shape) that are spatially separated from one another within the chamber 14. The library fragments released from a particular complex captured on the flow cell 10 or the library fragments formed in situ on the flow cell 10 may randomly distribute within the chamber 14 (as opposed to being confined within depressions 16 in the chamber 14). An example of this flow cell architecture is shown in FIGS. 5(i)-5(iii).

As another example, the flow cell 10 may include capture sites 22 without chambers 14 or depressions 16. In these examples, the capture sites 22 may be positioned in a desirable geometry across the substrate, and the primers 20 may be attached to a surface of the substrate 12 around the capture sites 22. The library fragments released from a particular complex captured on the flow cell 10 or the library fragments formed in situ on the flow cell 10 may randomly distribute on the substrate 12, and confinement of the released library fragments may be achieved by controlling reaction-diffusion.

As still another example, the flow cell 10 may include depressions 16 and capture sites 22, but no chambers 14. In these examples, the capture sites 22 may be positioned in a desirable geometry across the substrate 12, and the primers 20 may be attached within each of the depressions 16 as described herein. The library fragments released from a particular complex captured on the flow cell 10 or the library fragments formed in situ on the flow cell 10 may randomly distribute in depressions 16 near the complex, and confinement of the released library fragments may be achieved by controlling reaction-diffusion.

In still other examples, the capture sites 22 are not be included because the walls of the chambers 14 have a height that is sufficient to trap one or more of the complexes or samples introduced to the flow cell 10. A height that is sufficient to trap one or more of the complexes or samples corresponds to a chamber depth that is at least about 50% of an average diameter of the complexes or samples to be introduced to the flow cell 10. In an example, the height of the walls or the depth of the chamber 14 is 10 µm or more. In this example, the number/amount of complexes or samples in a given chamber 14 is random and will be determined by the Poisson distribution.

In any of the examples disclosed herein, it is to be understood that the primers 20 may not be located on depression 16 and/or chamber 14 sidewalls, in part because the layer 26 may not be located on the sidewalls. This helps to prevent the library fragments from seeding on the sidewalls.

The flow cell architecture disclosed herein may be used in a variety of applications, including sequencing techniques, such as a linked-long read sequencing application, high throughput protein biomarker studies, microbiome studies, or single cell omics. For example, the flow cell architecture and methods disclosed herein may be used to analyze binding of antibodies labeled with DNA. In this example, an antibody label is attached to a unique DNA sequence with P5/P7 adapters, which is introduced into the flow cell architecture. The antibody can be cleaved, and the released P5/P7 primers are seeded onto the flow cell. The seeded primers enable the identification of which antibody was attached.

Complexes for use with the flow cell architecture

The flow cell architecture may be particularly suitable for use with examples of the complexes disclosed herein. As noted herein, a complex includes a carrier (e.g., a hydrogel support or a solid support) and sequencing-ready nucleic acid fragments attached to or contained within the carrier. Examples of suitable complexes are shown in FIGS. 4A through 4C. While some example methods for making the complexes are described, it is to be understood that other methods may be used as long as sequencing-ready nucleic acid fragments attached to or contained within the carrier.

FIG. 4A illustrates a complex 40A that includes a solid support 42 and sequencing-ready nucleic acid fragments 44 attached to the solid support 42.

In one example, to form this complex 40A, an adapter sequence (52, 52') is bound to the solid support 42 through one member 46 of a binding pair. In an example, this adapter sequence includes a first sequencing primer sequence (e.g., a read 1 sequencing primer sequence), a first sequence (e.g., a P5' sequence) that is complementary to at least a portion of one of the primers 20 on the flow cell 10A-10I. As mentioned, this adapter sequence is bound to the one member 46 of the binding pair (e.g., biotin) so that it can be bound to the surface of the solid support 42 (which includes the other member (e.g., avidin, streptavidin, etc.) of the binding pair). This adapter sequence may also include an index sequence.

A Y-adapter may be mixed with a transposase enzyme (e.g., two Tn5 molecules) to form a transposome. The Y-adapter may include two mosaic end sequences that are hybridized to each other. One of the mosaic end sequences may be attached to a second sequencing primer sequence (e.g., a read 2 sequencing primer sequence), a second sequence (e.g., a P5' sequence) that is complementary to at least a portion of one of the primers 36 on the flow cell 10A-10I, and optionally an index/barcode sequence. Together, the second sequencing primer sequence and the second sequence make up adapter sequences 48, 48'.

A tagmentation process may then be performed. A fluid (e.g., a tagmentation buffer) including a sample (e.g., DNA) may be added to the transposomes and to the solid support 42 having the adapter sequence bound thereto. As the sample contacts the transposomes, the DNA is tagmented (fragmented and tagged with the adapter sequence 52, 52' on the solid support 42) and is bound to the Y-adapter (e.g., through ligation of the free mosaic end sequence). Successive tagmentation of the sample results in a plurality of bridged molecules between transposomes. To complete the sequencing ready fragments, further extension and ligation is undertaken to ensure fragments 50, 50' are attached to sequences 48 and 48'. The transposase enzyme may then be removed via sodium dodecyl sulfate (SDS) treatment or heat or proteinase K digestion.

The resulting complex 40A is shown in FIG. 4A. The bridged molecules are the sequencing-ready nucleic acid fragments 44, each of which includes a fragment 50, 50' and adapter sequences 48 and 52 or 48' and 50' attached at either end. The adapter sequences 52, 52' are those initially bound to the solids support 42, and include the first sequencing primer sequence, the first sequence complementary to the flow cell primer, and the one member 46 of a binding complex. The adapter sequences 48, 48' are from the Y-adapter, and include the second sequence complementary to another flow cell primer and the second sequencing primer sequence. Because each sequencing-ready nucleic acid fragment 44 includes suitable adapters for amplification (e.g., bridge amplification) and sequencing, PCR amplification is not performed. These fragments 44 are thus sequencing-ready. Moreover, because the library fragments 44 are from the same sample, the fragments 44 may be suitable for linked long read applications.

FIG. 4B illustrates another complex 40B that includes a solid support 42 and sequencing-ready nucleic acid fragments 44' attached to the solid support 42. In one example, a PCR-free nucleotide library is created in a tube, and then the library is hybridized to the solid support 42 in the tube. In the example shown in FIG. 4B, primers having one member of a binding pair are added to the library fragments in the tube, and then the sequencing-ready nucleic acid fragments 44' are bound to the solid support 42. In another example, the solid support 42 may have primers attached thereto via a binding pair (e.g., avidin on the support 42 and biotin attached to the primer). These primers hybridize to library fragments (and thus the primer and binding pair member are at one end of the fragments and not at the other). In another example, extension may be performed using a strand displacing enzyme. This will result in an entirely double stranded library (e.g., no fork or Y-adapter, as shown in FIG. 4B). The sequencing-ready nucleic acid fragments 44' may be released on the flow cell via denaturation. Because the library fragments 44' are created prior to being attached to the solid support 42, the fragments 44' may not be from the same sample, and thus may not be suitable for linked long read applications.

FIG. 4C illustrates an example of the complex 40C that includes a hydrogel support 70 and sequencing-ready nucleic acid fragments 44" contained within the hydrogel support 70.

To form this complex 40C, a fluid containing hydrogel monomer(s) and/or polymer(s) and crosslinker(s) are mixed in the presence of the sample (e.g., genetic material). This fluid may be loaded into mineral oil or another suitable hydrophobic fluid, and emulsified to generate droplets. A radical initiator may be added to polymerize and/or crosslink the hydrogel monomer(s) and/or polymer(s) and form the hydrogel support 70. Examples of suitable monomers, polymers, crosslinkers, and initiators are described in reference to FIGS. 5(*i*)-(*iii*).

The sample becomes encapsulated within the hydrogel support because its size is sufficient that it cannot pass through the pores of the hydrogel bead. In some examples, the sample is DNA or RNA and is at least about 100 nucleotides in length (e.g., 1,000 nucleotides or more, 10,000 nucleotides or more, 500,000 nucleotides or more, etc.). In some examples, the pore size of the hydrogel support 70 refers to an average diameter or an average effective diameter of a cross-section of the pores, based on a measurement of a plurality of pores. The effective diameter of a cross-section that is not circular equals the diameter of a circular cross-section that has the same cross-sectional area as that of the non-circular cross-section. In an example, the pore size ranges from about 10 nm to about 100 nm.

Library preparation can then take place within the hydrogel support 70. Multiple reagent exchange may take place through the pores of the hydrogel support 70. The sample and any library fragments generated therefrom are maintained within the hydrogel matrix. Library preparation may involve fragmenting the sample and adding adapters that will result in sequence-ready fragments 44".

In an example, library preparation may be performed via tagmentation that takes place within the hydrogel support 70. The resulting complex 40C is shown in FIG. 4C. The adapter sequences include suitable adapters for bridge amplification and sequencing and thus the resulting fragments 44" are sequencing-ready. In another example, library preparation may be performed using polymerase extension, which results in a double stranded library. This example library needs to be denatured prior to release form the hydrogel support 70 and seeding.

Methods Involving Complexes

Some examples of the method disclosed herein utilize an example of the flow cell 10 disclosed herein and any one of the complexes 40A, 40B, or 40C. As described above, each of the complexes 40A, 40B, or 40C includes sequence-ready fragments obtained from the same sample of genetic material. When one or a few of the complexes are isolated within the respective chambers, spatial co-localization of the libraries from the same sample is achieved.

In a first example method, the flow cell 10 includes the plurality of chambers 14, but does not include the capture sites 22. Rather, the chamber 14 itself functions as the capture site for the complex(es) 40A, 40B, or 40C introduced to the flow cell. Each chamber 14 can function as a capture site, for example, when the depth is at least about 50% of an average diameter of the complex(es) 40A, 40B, or 40C that are to be introduced thereto. In an example, the depth is at least about 10 μm (about 10 μm or more). In this example, the flow cell 10 may have the primers 20 attached to the bottom surface of the chamber 14, or may include the depressions 16 with the primers 20 contained therein. In these examples, the number of complex(es) 40A, 40B, or 40C that become trapped in any given chamber 14 may be random and determined by the Poisson distribution.

In this first example method, the complexes 40A, 40B, or 40C are introduced into the flow cell 10, for example through one or more input ports. The complexes 40A, 40B, or 40C may be introduced into a fluid, such as such as Tris-HCl buffer or 0.5× saline sodium citrate (SSC) buffer. At least some complexes 40A, 40B, or 40C from the fluid will settle into at least some of the chambers 14. It is to be understood that some complexes 40A, 40B, or 40C may not settle, and these complexes 40A, 40B, or 40C will be removed from the flow cell before further processes are performed. It is also to be understood that some chambers 14 may receive one or more of the complexes 40A, 40B, or 40C, while others of the chambers 14 may receive no complexes 40A, 40B, or 40C. The complex 40A, 40B, or 40C distribution in this example is random, in part because of the lack of capture sites 22.

This first example method then includes washing away non-trapped complexes 40A, 40B, or 40C from the flow cell. Washing may involve introducing the fluid into the flow cell 10. The flow may push any complexes 40A, 40B, or 40C that have not settled out through an exit port of the flow cell. The deep chambers 14 may prevent any settled complexes 40A, 40B, or 40C from becoming part of the exit flow.

This example of the method then includes causing the carrier (e.g., the solid support 42 or the hydrogel support 70) of the trapped complexes 40A, 40B, or 40C to release the sequencing-ready nucleic acid fragments 44, 44', or 44" into the respective chamber 14 in which each complex 40A, 40B, or 40C is trapped. In this example, transport and seeding of the sequencing-ready nucleic acid fragments 44, 44', or 44" are restricted by the depth of the respective chamber 14, and thus an external immobilizing agent is not introduced to the flow cell.

Causing the carrier (i.e., support 42 or 70) to release the sequencing-ready nucleic acid fragments 44, 44', or 44" may vary, depending upon the complex 40A, 40B, or 40C that is used. In one example, the carrier is the solid support 42, and the causing involves introducing a cleaving agent to the flow cell. The cleaving agent may initiate chemical, enzymatic, or photo-chemical release of the sequencing-ready nucleic acid fragments 44, 44' from the solid support 42. In these examples, another stimulus, such as heat or light, may trigger the cleaving agent to release the library fragments 44 or 44' from the solid support 42. As one example, free biotin may be introduced as the cleaving agent, and heating to about 92° C. may be used to induce biotin-oligo release from the solid support 42.

In other examples, the complex 40C is used and thus the carrier is the hydrogel support 70. In these other examples, causing library release may involve heating the flow cell 10, introducing a cleaving agent to the flow cell 10, or combinations thereof. Heating to release the library fragments 44" from the hydrogel support 70 may involve heating to a temperature of about 90° C. The entire flow cell 10 may be heated, and when the complexes 40C heat up, the hydrogel support 70 may degrade to release the fragments 44". In some examples, the cleaving agent may include one or more components that can depolymerize the hydrogel support 70 and release the sequencing-ready fragments 44" therefrom. As examples, the cleaving agent includes dithiothreitol (DTT), tris-(2-carboxyethyl)phosphine (TCEP), or tris-(3-hydroxypropyl)phosphine (THP). In other examples, the cleaving agent is light. In these examples, the crosslinker used to form the hydrogel support 70 may include a photo-cleavable moiety, and exposure of the complexes 40C in the chambers 14 to light of an appropriate wavelength can cleave this moiety and degrade the hydrogel support 70.

As mentioned, transport and seeding of the sequencing-ready nucleic acid fragments 44, 44', or 44" are restricted by the depth of the respective chambers 14. As such, the fragments 44, 44', or 44" of any particular complex 40A, 40B, or 40C will be confined to the chamber 14 to which the particular complex 40A, 40B, or 40C is confined.

With the flow cell architecture disclosed herein, the primers 20 on the surface of the flow cell 10 can seed the released sequencing-ready nucleic acid fragments 44, 44', or 44". In an example, seeding is accomplished through hybridization between the first or second sequence of the fragment 44, 44', or 44" and a complementary one of the primers 20 with the chamber 14. Seeding may be performed at a suitable hybridization temperature for the fragment 44, 44', or 44" and the primer(s) 20.

The location at which the sequencing-ready nucleic acid fragments 44, 44', or 44" seed within the respective chambers 14 depends, in part, upon how the primers 20 are attached within the chamber 14. In some examples of the flow cell 10, each chamber 14 has a bottom surface, and either the primers 20 are attached to a polymer layer 26 across the bottom surface, or the primers 20 are respectively attached to a plurality of spatially segregated polymer islands positioned on the bottom surface. In these examples, respectively, the sequencing-ready nucleic acid fragments 44, 44', or 44" seed across the bottom surface of the chamber 14, or across each of the islands. In other examples, each chamber 14 has a bottom surface and a plurality of depressions 16 defined therein, and the primers 20 are respectively attached to a polymer layer 26 within each of the depressions 16. In these examples, the sequencing-ready nucleic acid fragments 44, 44', or 44" seed across the polymer layer 26 within each of the depressions 16.

In another example method (referred to as a second example method), the flow cell 10 includes the plurality of chambers 14, the capture site 22 within each of the plurality of chambers 14; and the primers 20 attached within each of the plurality of chambers 14. In this example, the flow cell 10 may or may not include the depressions 16.

In this second example method, the depth of each chamber 14 is 5 µm or less. With such a shallow depth, the capture site 22 may be included to immobilize a single complex 40A, 40B, or 40C in a single chamber 14. While each chamber 14 has a capture site 22, it is to be understood that some of the chambers 14 may not receive a complex 40A, 40B, or 40C during any given run of the method.

In this second example method, the complexes 40A, 40B, or 40C are introduced into the flow cell 10, for example through one or more input ports. The complexes 40A, 40B, or 40C may be introduced into a fluid, such as the buffers disclosed herein. In this example, respective capture sites 22 and complexes 40A, 40B, or 40C are members of a binding pair, so that one complex 40A, 40B, or 40C binds to one capture site 22 within each of the chambers 14. More specifically, the capture sites 22 may include the first member of the binding pair and each of the complexes 40A, 40B, or 40C may include the second member of the binding pair. As one specific example, the capture site 22 is a capture site primer (e.g., a capture oligonucleotide), and each of the complexes 40A, 40B, or 40C includes a complementary primer that can hybridize to the capture site primer. As another specific example, the capture site 22 may include avidin, and biotin may be attached to the surface of the complex 40A, 40B, or 40C.

This second example method then includes washing away non-immobilized complexes 40A, 40B, or 40C from the flow cell 10. Washing may involve introducing any suitable buffer into the flow cell 10. The flow may push any complexes 40A, 40B, or 40C that have not attached to the capture sites 22 out through an exit port of the flow cell 10.

This second example method then includes introducing an external immobilization agent to the flow cell 10, and specifically, to the plurality of chambers 14. In an example, the external immobilization agent is air, or a liquid medium or a viscous medium that is not miscible with the complexes 40A, 40B, or 40C of the fluid that have been introduced to the flow cell chambers 14.

Using air to aspirate the washing fluid out of the flow cell 10 can create a liquid droplet that surrounds the complexes 40A, 40B, or 40C and forms a diffusion barrier. The liquid or viscous external immobilization agent at least partially surrounds the complexes 40A, 40B, or 40C that are attached within the chambers 14. By at least partially surrounding the complexes 40A, 40B, or 40C, the external immobilization agent inhibits diffusion of the sequencing-ready nucleic acid fragments 44, 44', or 44" outside of the chambers 14 when the fragments 44, 44', or 44" are released. When the external immobilization agent is a temperature responsive material, raising the temperature to the seeding temperature may render the agent more viscous and in a form that can prevent library diffusion.

It is to be understood that any of the external immobilization agents disclosed herein may be used, but in one example, the external immobilization agent is a liquid diffusion barrier selected from the group consisting of mineral oil and silicone oil, a viscous medium diffusion barrier selected from the group consisting of glycerol and sucrose, and combinations thereof.

This example of the method then includes causing the carrier (e.g., the solid support 42 or the hydrogel support 70) of the trapped complexes 40A, 40B, or 40C to release the sequencing-ready nucleic acid fragments 44, 44', or 44" into the respective chamber 14 in which each immobilized 40A, 40B, or 40C is trapped. In this example, transport and seeding of the sequencing-ready nucleic acid fragments 44, 44', or 44" are restricted by the external immobilization agent.

Causing the carrier (i.e., support 42 or 70) to release the sequencing-ready nucleic acid fragments 44, 44', or 44" may vary, depending upon the complex 40A, 40B, or 40C that is used. In one example, the carrier is the solid support 42, and the causing involves introducing a cleaving agent to the flow cell 10 (as described in the first example method), and using another stimulus to trigger the cleaving agent to release the library fragments 44 or 44' from the solid support 42. In other examples, the complex 40C is used and thus the carrier is the hydrogel support 70. In these other examples, causing library release may involve heating the flow cell, introducing a cleaving agent to the flow cell, or combinations thereof (as described in the first example method).

As mentioned, transport and seeding of the sequencing-ready nucleic acid fragments 44, 44', or 44" in this second example method are restricted by the external immobilization agent. As such, the fragments 44, 44', or 44" of any particular complex 40A, 40B, or 40C will be confined to the chamber 14 to which the particular complex 40A, 40B, or 40C is confined because the external immobilization agent at least partially surrounds the complex 40A, 40B, or 40C.

With the flow cell architecture disclosed herein, the primers 20 on the surface of the flow cell 10 can seed the released sequencing-ready nucleic acid fragments 44, 44', or 44". Seeding is accomplished through hybridization between the first or second sequence of the fragment 44, 44', or 44" and a complementary one of the primers 20 with the chamber 14. Seeding may be performed at a suitable hybridization temperature for the fragment 44, 44', or 44" and the primer(s) 20.

The location at which the sequencing-ready nucleic acid fragments 44, 44', or 44" seed within the respective chambers 14 depends, in part, upon how the primers 20 are attached within the chamber 14. In some examples of the flow cell, each chamber 14 has a bottom surface, and either the primers 20 are attached to a polymer layer 26 across the bottom surface, or the primers 20 are respectively attached to a plurality of spatially segregated polymer islands positioned on the bottom surface. In these examples, respectively, the sequencing-ready nucleic acid fragments 44, 44', or 44" seed across the bottom surface of the chamber 14, or across each of the islands. In other examples, each chamber 14 has a bottom surface and a plurality of depressions defined therein, and wherein the primers are respectively attached to a polymer layer 26 within each of the depressions 16. In these examples, the sequencing-ready nucleic acid fragments 44, 44', or 44" seed across the polymer layer 26 within each of the depressions 16.

In still another example of the method (referred to as the third example method), any example of the flow cell 10 shown in FIGS. 1, 2A, 2B, and 3A-3C may be used. In this third example method, the capture site 22 may be included to immobilize a single complex 40A, 40B, or 40C in a single chamber 14, and the depth of each chamber 14 may be sufficient to restrict transport and seeding of the sequencing-ready nucleic acid fragments 44, 44', or 44" to respective depressions 16 within each of the respective chambers 14.

In this third example method, the complexes 40A, 40B, or 40C are introduced into the flow cell 10, for example through one or more input ports. The complexes 40A, 40B, or 40C may be introduced into a fluid, such as the buffers disclosed herein. In this example, respective capture sites 22 and complexes 40A, 40B, or 40C are members of a binding pair, so that one complex 40A, 40B, or 40C binds to one capture site 22 within at least some of the chambers 14. While each chamber 14 has a capture site 22, it is to be understood that some of the chambers 14 may not receive a complex 40A, 40B, or 40C during any given run of the method.

This third example method then includes washing away non-trapped complexes 40A, 40B, or 40C from the flow cell 10. Washing may involve introducing a buffer into the flow cell. The flow may push any complexes 40A, 40B, or 40C that have not been immobilized at a capture site 22 out through an exit port of the flow cell 10.

This example of the method then includes causing the carrier (e.g., the solid support 42 or the hydrogel support 70) of the trapped complexes 40A, 40B, or 40C to release the sequencing-ready nucleic acid fragments 44, 44', or 44" into the respective chamber 14 in which each complex 40A, 40B, or 40C is trapped. In this example, transport and seeding of the sequencing-ready nucleic acid fragments 44, 44', or 44" are restricted by the depth of the respective chambers 14, and thus an external immobilizing agent is not introduced to the flow cell 10.

Causing the carrier (i.e., support 42 or 70) to release the sequencing-ready nucleic acid fragments 44, 44', or 44" may vary, depending upon the complex 40A, 40B, or 40C that is used. In one example, the carrier is the solid support 42, and the causing involves introducing a cleaving agent to the flow cell 10 (as described in the first example method) and exposing the flow cell 10 to an external stimulus. In other examples, the complex 40C is used and thus the carrier is the hydrogel support 70. In these other examples, causing library release may involve heating the flow cell, introducing a cleaving agent to the flow cell, or combinations thereof (as described in the first example method).

As mentioned, transport and seeding of the sequencing-ready nucleic acid fragments 44, 44', or 44" are restricted by the depth of the respective chambers 14. As such, the fragments 44, 44', or 44" of any particular complex 40A, 40B, or 40C will be confined to the chamber 14 to which the particular complex 40A, 40B, or 40C is confined. In this particular example, because the flow cell 10 includes the primers 20 in the depressions 16, the seeding of the fragments 44, 44', or 44" takes place within the depressions 16 and not on the interstitial regions 24.

In another example method (referred to as a fourth example method), the flow cell 10 may be any of the architectures disclosed herein, and includes at least the capture sites 22 and the primers 20.

Similar to the other methods disclosed herein, the complexes 40A or 40B (including the solid support 42) are introduced into the flow cell 10, for example through one or more input ports. The complexes 40A or 40B may be introduced into a fluid, such as the buffers disclosed herein. In this example, respective capture sites 22 and complexes 40A or 40B are members of a binding pair, so that one complex 40A or 40B binds to one capture site 22. More specifically, the capture sites 22 may include the first member of the binding pair and each of the complexes 40A or 40B may include the second member of the binding pair. As one specific example, the capture site 22 is a capture site primer (e.g., a capture oligonucleotide), and each of the complexes 40A or 40B includes a complementary primer that can hybridize to the capture site primer. As another specific example, the capture site 22 may include avidin, and biotin may be attached to the surface of the complex 40A or 40B.

This fourth example method then includes introducing an external immobilization agent to the flow cell 10.

In one example, the external immobilization agent is air. Introducing air into the flow cell 10 aspirates most of the fluid (in which the complexes 40A or 40B had been introduced) and also pushes any non-immobilized complexes 40A or 40B out of the flow cell 10. The immobilized complexes 40A or 40B serve as liquid pinning centers, and thus retain some of the liquid from the fluid at their respective surfaces. The retained liquid forms a droplet that surrounds each complex 40A or 40B. In some examples, droplet is a liquid film having a shape that resembles a tent (e.g., with its height at the center set by the seeding particle and the meniscus profile set by the strong surface tension of the liquid). This liquid droplet creates a diffusion barrier for library fragments 44, 44' that are released from the complex 40A or 40B.

In some examples, the liquid droplets that are formed around the complexes 40A or 40B may be contiguous, and thus may be form a shallow liquid layer across the flow cell surface. In other examples, the liquid droplets that are formed around the complexes 40A or 40B may be spatially isolated from one another. In still other examples, some of the liquid droplets are contiguous and form liquid islands that are spatially isolated from other islands of contiguous liquid droplets. A shallow liquid layer is more likely to form when the density of the complexes 40A or 40B on the flow cell surface is increased.

The configuration of the droplets may be controlled by selecting a solid support 42 with a desirable diameter, applying the complexes 40A or 40B at a particular surface density, adjusting the flow rate and/or speed of the air through the flow cell 10, and selecting the fluid so that it has desired physical properties (e.g., viscosity, surface tension, etc.). For example, more complexes 40A or 40B immobilized within the flow cell 10 (e.g., higher surface density) leads to a shallow liquid layer with a more uniform thickness. In contrast, when fewer complexes 40A or 40B are immobilized within the flow cell 10, the liquid droplets tend to be isolated from one another or to form islands of liquid (e.g., small, separated puddles that surround respective groups of complexes 10A or 10B).

The air may be introduced into the flow cell 10 at a predetermined flow rate. In an example, the flow rate ranges from about 100 μL/min to about 2000 μL/min. As mentioned, the air flow may be adjusted to alter the configuration of the droplets. For example, the air flow rate may influence the size and/or diameter of liquid around the complexes 40A or 40B. As an example, a higher air flow rate may lead to a continuous shallow liquid layer, while a lower air flow rate may lead to liquid droplets that are isolated from one another or that form several islands of liquid.

The physical properties of the fluid can also alter the configuration of the liquid droplets. For example, higher surface tension fluids have a greater affinity to adhere to the surface of the complexes 40A or 40B, which leads to greater wetting and a bigger meniscus. In some instances, the fluid used to introduce the complexes 40A or 40B may be selected to have a surface tension ranging from about 20 mN•m$^{-1}$ to about 90 mN•m$^{-1}$. As examples, a 6M NaCl solution has a surface tension of about 83 mN•m$^{-1}$; a 55% aqueous sucrose solution has a surface tension of about 76 mN•m$^{-1}$; water has a surface tension of 72.86 mN•m$^{-1}$; water with an added surfactant may have a surface tension ranging from 20 mN•m$^{-1}$ to about 72 mN•m$^{-1}$; and ethanol has a surface tension of 22.39 mN•m$^{-1}$. The surface tension may vary, however, depending upon the fluid used to introduce the complexes 40A or 40B.

The peak height of any of the liquid droplets (in the form of isolated droplets, puddle islands, or a liquid layer) is less than the height of the complex 40A or 40B. In an example, the peak height of any of the liquid droplets (in the form of isolated droplets, puddle islands, or a liquid layer) is about 3 μm or less. The shallow height of the liquid droplets forces the released library fragments to diffuse along the X-Y plane of the flow cell 10, rather than throughout the entire flow channel where they become captured by the surface primers 20. This can result in improved localization of the library fragments near the complex 40A, 40B from which they are released.

In another example, the external immobilization agent is a liquid medium or a viscous medium that is not miscible with the complexes 40A or 40B that have been introduced to the flow cell 10. In this example, prior to introducing the liquid or viscous medium, the non-immobilized complexes 10A or 10B may be washed away from the flow cell 10. Washing may involve introducing any suitable buffer into the flow cell 10. The flow may push any complexes 40A or 40B that have not attached to the capture sites 22 out through an exit port of the flow cell 10.

The liquid or viscous external immobilization agent may be introduced in an amount that will form a shallow layer (e.g., about 3 μm or less) that at least partially surrounds the complexes 40A or 40B that are attached within the flow cell 10. By at least partially surrounding the complexes 40A or 40B, the external immobilization agent inhibits diffusion of the sequencing-ready nucleic acid fragments 44, 44', or 44" outside of the shallow layer. When the external immobilization agent is a temperature responsive material, raising the temperature to the seeding temperature may render the agent more viscous and in a form that can prevent library diffusion.

This example of the method then includes causing the carrier (e.g., the solid support 42) of the immobilized complexes 40A or 40B to release the sequencing-ready nucleic acid fragments 44, 44', or 44". As one example, a cleaving agent may be introduced to the flow cell 10 (as described in the first example method), and another stimulus may be applied to trigger the cleaving agent to release the library fragments 44 or 44' from the solid support 42. In this example, transport and seeding of the sequencing-ready nucleic acid fragments 44, 44', or 44" are restricted by the liquid droplets formed around the complexes 40A or 40B.

With the flow cell architecture disclosed herein, the primers 20 on the surface of the flow cell 10 can seed the released sequencing-ready nucleic acid fragments 44, 44', or 44" as described herein.

In any of the examples of the method involving the complexes 40A, 40B, or 40C (e.g., the first, second, third or fourth methods described herein), the seeded sequencing libraries can be amplified using cluster generation.

In one example of cluster generation, the sequencing-ready nucleic acid fragments 44, 44', or 44" are copied from the hybridized primers 20 by 3' extension using a high-fidelity DNA polymerase. The original sequencing-ready nucleic acid fragments 44, 44', or 44" are denatured, leaving the copies immobilized within the chambers 14. Isothermal bridge amplification or some other form of amplification may be used to amplify the immobilized copies. For example, the copied templates loop over to hybridize to an adjacent, complementary primer 20, and a polymerase copies the copied templates to form double stranded bridges, which are denatured to form two single stranded strands. These two strands loop over and hybridize to adjacent, complementary primers 20 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. It is to be understood that clustering results in the formation of several template sequencing-ready nucleic acid fragments, e.g., in each chamber 14, and in some instances, within each depression 16 within each chamber 14. This example of clustering is bridge amplification, and is one example of the amplification that may be performed. It is to be understood that other amplification techniques may be used, such as the exclusion amplification (ExAmp) workflow (Illumina Inc.).

After cluster generation, sequencing may be performed. Any example of the flow cell 10 disclosed herein may be used in a variety of sequencing approaches or technologies, including techniques often referred to as sequencing-by-synthesis (SBS), cyclic-array sequencing, sequencing-by-ligation, pyrosequencing, and so forth.

As one example, a sequencing by synthesis (SBS) reaction may be run on a system such as the HISEQ™, HISEQX™, MISEQ™, MISEQDX™, MINISEQ™, NOVASEQ™, NEXTSEQDX™, ISEQ™, NEXTSEQ™, or other sequencer systems from Illumina (San Diego, Calif.).

A sequencing primer may be introduced that hybridizes to a complementary sequence on the template polynucleotide strand. This sequencing primer renders the template polynucleotide strand ready for sequencing. In SBS, extension of the sequencing primers along the template sequencing-ready nucleic acid fragments (the template polynucleotide strand) is monitored to determine the sequence of nucleotides in the templates. The 3'-ends of the templates and any flow cell-bound primers 20 (not attached to the copied) may be blocked to prevent interference with the sequencing reaction, and in particular, to prevent undesirable priming. The underlying chemical process can be polymerization (e.g., catalyzed by a polymerase enzyme) or ligation (e.g., catalyzed by a ligase enzyme).

In a particular polymerase-based SBS process, fluorescently labeled nucleotides are added to the sequencing primer (thereby extending the sequencing primer) in a template dependent fashion such that detection of the order and type of nucleotides added to the sequencing primer can be used to determine the sequence of the template. More particularly, one of the nucleotides is incorporated, by a respective polymerase, into a nascent strand that extends the sequencing primer and that is complementary to the template polynucleotide strand. For example, to initiate a first SBS cycle, one or more labeled nucleotides, DNA polymerase, etc., may be delivered into/through the flow cell 10, etc., where sequencing primer extension causes a labeled nucleotide to be incorporated. This incorporation can be detected through an imaging event. During an imaging event, an illumination system (not shown) may provide an excitation light to the flow cell 10.

In some examples, the fluorescently labeled nucleotides can further include a reversible termination property that terminates further primer extension once a nucleotide has been added to the template. For example, a nucleotide analog having a reversible terminator moiety can be added to the template such that subsequent extension cannot occur until a deblocking agent is delivered to remove the moiety. Thus, for examples that use reversible termination, a deblocking reagent can be delivered to the flow cell, etc. (after detection occurs).

Wash(es) may take place between the various fluid delivery steps. The SBS cycle can then be repeated n times to extend the template by n nucleotides, thereby detecting a sequence of length n.

While SBS has been described in detail, it is to be understood that the flow cells 10 described herein may be utilized with other sequencing protocol, for genotyping, or in other chemical and/or biological applications.

Methods Involving Complex Formation on the Flow Cell Architecture

Other examples of the methods disclosed herein do not utilize the complexes 40A, 40B, or 40C shown in FIGS. 4A through 4C. Rather, a hydrogel matrix is formed in situ within the chambers 14 of the flow cell. This example will be described in reference to FIGS. 5(i)-5(iii).

In this example, the flow cell 10' may be part of a sequencing kit that includes the flow cell 10' and the various reagents to form the hydrogel matrix 74 within the chambers 14 of the flow cell 10'. An example of the sequencing kit includes the flow cell 10', which includes the plurality of chambers 14 (e.g., formed in or on a substrate 12 as described in reference to FIGS. 1, 2A and 2B), and primers 20 attached within each of the plurality of chambers 14. In the example shown in FIGS. 5(i)-5(iii), each chamber has a bottom surface and the primers 20 are attached to the polymer layer 26 across the bottom surface. While not shown, the polymer layer 26 (on the bottom chamber surface) could alternatively be in the form of a plurality of spatially segregated polymer islands, and the primers 20 would be respectively attached to each of the islands. In still another example of the flow cell 10', a plurality of depressions 16 (as defined herein for the flow cell 10) may be defined in the bottom surface of the chamber, and the primers 20 would be attached to the polymer layer 26 in each of the depression 16.

As shown in FIG. 5(i), the flow cell 10' also includes an example of the capture site 22', where the capture site 22' is configured to capture a sample 72.

The capture site 22' may be any example of the chemical capture agent disclosed herein that can attach to the sample 72 that is introduced to the flow cell 10'. For a native DNA or RNA sample 72, the capture site 22' may include linkers having a nucleic acid binding moiety on one end, such as intercalators that bind via charge or hydrophobic interaction, or one member of a binding pair (where the sample 72 include the other member), or oligonucleotides that can hybridize to the sample 72, etc. For a cell sample 72, a linker may include a cell membrane binding moiety (e.g., antigens against surface proteins) or a membrane penetrating moiety (e.g., phospholipids on one end).

While not shown in FIGS. 5(i)-5(iii), the flow cell 10' may include depressions 16 within each of the chambers 14, and primers 20 may be attached within each of the depressions 16.

The sequencing kit also includes an encapsulation (hydrogel) matrix precursor composition consisting of a fluid, a monomer or polymer including a radical generating and chain elongating functional group, a radical source, and a crosslinker. The encapsulation (hydrogel) matrix precursor composition does not include the sample 72. In an example, the encapsulation (hydrogel) matrix precursor composition includes from about 2% (w/v) to about 20% (w/v) of the monomer(s) or polymer(s), from about 1 wt % to about 10 wt % of the crosslinker, and from about 0.1% (w/v) to about 10% (w/v) of the radical source. When included in the composition, the radical initiator may be present in an amount of from about 0.1% (w/v) to about 10% (w/v).

The fluid of the encapsulation (hydrogel) matrix precursor composition may be water (e.g., deionized water).

When the monomer is used in the encapsulation (hydrogel) matrix precursor composition, the monomer is selected from the group consisting of acrylamide, N,N'-bis(acryloyl) cystamine, bisacrylamide, diacrylate, diallylamine, triallylamine, divinyl sulfone, ethyleneglycol diallyl ether, ethyleneglycol diacryate, trimethylolpropane trimethacrylate, ethoxylated trimethylol diacrylate, ethoxylated pentaerythritol tetracrylate, a collagen monomer, and combinations thereof. When the polymer is used in the encapsulation (hydrogel) matrix precursor composition, the polymer is selected from the group consisting of polyethylene glycol-thiol, polyethylene glycol-acrylate, polyethylene glycol diacrylate, polyethylene glycol (e.g., having a weight average molecular weight ranging from about 100 to about 200,000), polypropylene oxide, polyacrylic acid, poly(hydroxyethyl methacrylate), poly(methyl methacrylate), poly(N-isopropylacrylamide), poly(lactic acid), poly(lactic-co-glycolic acid), polycaprolactone, poly(vinylsulfonic acid), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, a collagen polymer, and combinations thereof. Any of the monomer(s) and polymer(s) may be also be used in combination within the encapsulation (hydrogel) matrix precursor composition.

The radical source is a molecule that generates radicals when broken down. In an example, the radical source is selected from the group consisting of potassium persulfate, ammonium persulfate, 4,4'-azobis(4-cyanovaleric acid), 1,1'-azobis(cyclohexanecarbonitrile), azobisisobutyronitrile, 2,2'-azobis(2-methylpropionitrile), 2,2'-azobis(2-methylpropionitrile), peroxide, riboflavin, 3-(dimethylamino) propionitrile, and combinations thereof.

The crosslinker forms bonds, e.g., disulfide bonds, in the polymer of the hydrogel matrix. The crosslinker may be reversible, in that it can be crosslinked and uncrosslinked depending on the chemical to which it is exposed. In example, the reversible crosslinker is a bisacrylamide crosslinker containing disulfide bonds, which can be broken down with reducing agents, such as DTT, TCEP, or THP (phosphine). In an example, the crosslinker is selected from the group consisting of acrylamide, N,N'-bis(acryloyl)cystamine, bisacrylamide, 1,4-diacroylpiperazine, N-N'-diallyl L-tartardiam ide, and N-N'-(1,2-dihydroxyethylene)-bis-acrylamide.

The sequencing kit also includes a radical initiator as part of the encapsulation matrix precursor composition or as a separate component. In an example, the radical initiator may be a photoinitiator. Examples of photoinitiators include azobisisobutyronitrile, benzoyl peroxide, eosin-5-isothiocyanate. This type of radical initiator may be included in the encapsulation (hydrogel) matrix precursor composition because it will not initiate crosslinking until exposed to light of an appropriate wavelength. In another example, the radical initiator may initiate crosslinking when exposed to the radical source in the encapsulation (hydrogel) matrix precursor composition. In these examples, the radical initiator is maintained separate from the encapsulation (hydrogel) matrix precursor composition until it is desirable to form the hydrogel matrix on the flow cell 10'. An example of this type of radical initiator is tetramethylethylenediamine (TEMED).

In an example, the sequencing kit may further include a sample fluid including water and the sample 72 (e.g., genetic material).

In an example, the sequencing kit may further include a library preparation solution including adapter sequences and transposomes.

In an example of the method which uses the sequencing kit, the sample fluid (including the sample 72 of genetic material) is introduced to the flow cell 10', e.g., through an input port (FIG. 5(*i*)). Through the capture site(s) 22' in the respective chambers 14, at least some of the genetic material (sample 72) enters at least some of the plurality of chambers 14. The sample 72 immobilizes to the capture site(s) 22'.

The liquid of the sample fluid, including any unbound sample 72, may then be removed. Removal may involve introducing a wash buffer (e.g., TRIS HCl) into the flow cell 10'. The flow may push any unbound sample 72 out through an exit port of the flow cell 10'.

This example of the method includes introducing the encapsulation matrix precursor composition 76 into the flow cell 10' (FIG. 5(*ii*)). At least some of encapsulation matrix precursor composition 76 enters at least some of the chambers 14 containing the sample 72.

The method then includes encapsulating the sample 72 (i.e., genetic material) in a hydrogel matrix 74 in the at least some of the chambers 14 by initiating crosslinking or crosslinking and polymerization of the encapsulation matrix precursor composition 76 contained in the at least some of the chambers 14 (FIG. 5(*iii*)).

Prior to encapsulation, the external immobilization agent may be introduced into the flow cell 10'. This agent may remove the encapsulation matrix precursor composition 76 from the flow cell 10', except for the composition 76 that has entered the chambers. This creates a barrier 78 during the hydrogel matrix 74 formation. Any example of the external immobilization agent disclosed herein may be used.

When the encapsulation matrix precursor composition 76 includes a photoinitiator (e.g., an ultraviolet radical initiator), the encapsulation involves exposing the flow cell 10' to ultraviolet radiation. This exposure initiates radical generation, which in turn initiates crosslinking or crosslinking and polymerization of the components in the encapsulation matrix precursor composition 76 that remains in the chambers 14. Crosslinking or crosslinking and polymerization forms the hydrogel matrix 74 within the chambers 14. This encapsulates the sample 72 within the hydrogel matrix 74 within the chambers 14.

When a radical initiator is used that initiates crosslinking when exposed to the radical source, the radical initiator is introduced separately from the encapsulation matrix precursor composition 76. In these examples, the encapsulation involves exposing the flow cell 10' to the radical initiator. In this example, the radical initiator may be introduced with the external immobilization agent. The radical initiator in the external immobilization agent initiates radical generation in the encapsulation matrix precursor composition 76, which in turn initiates crosslinking or crosslinking and polymerization of the components in the encapsulation matrix precursor composition 76 that remains in the chambers 14. Crosslinking forms, or crosslinking and polymerization form the hydrogel matrix 74 within the chambers 14. This encapsulates the sample 72 within the hydrogel matrix 74 within the chambers 14.

Library preparation may take place on the flow cell 10' surface. The external immobilization agent may be removed, and a buffer may be introduced to the flow cell 10' along with the library preparation solution. Library preparation may take place as described in reference to FIG. 4C.

Seeding and cluster and sequencing may then be performed in accordance with the examples disclosed herein.

To further illustrate the present disclosure, examples are given herein. It is to be understood that these examples are provided for illustrative purposes and are not to be construed as limiting the scope of the present disclosure.

NON-LIMITING WORKING EXAMPLES

Example 1

A hydrophobic layer (CYTOP® S) was deposited on the outermost silicon layer of a silicon-on-insulator substrate, and a positive photoresist was deposited on the hydrophobic layer. Using photolithography, micro-chambers with 50 μm diameters were then patterned in the photoresist. The hydrophobic layer and the outermost silicon layer were then etched following the photoresist pattern. The photoresist was then lifted off.

The micro-chambers in the substrate were silanized, and PAZAM was deposited thereon. Non-attached PAZAM was washed away, and then P5 and P7 primers were grafted to the PAZAM in the micro-chambers. A lid was attached to the substrate.

Complexes similar to those shown in FIG. 4A were prepared having an average diameter of 3 μm. The fragments on a particular bead were from the same long DNA molecule (from the PhiX genome). The library fragments were attached to the solid support via a desthiobiotin oligo, which has weaker affinity than biotin to streptavidin on the bead surface. The library fragments included P5 and P7' sequences, along with index sequences, and read 1 and read 2 sequences. The complexes were loaded into the micro-chambers.

Figure 6C:
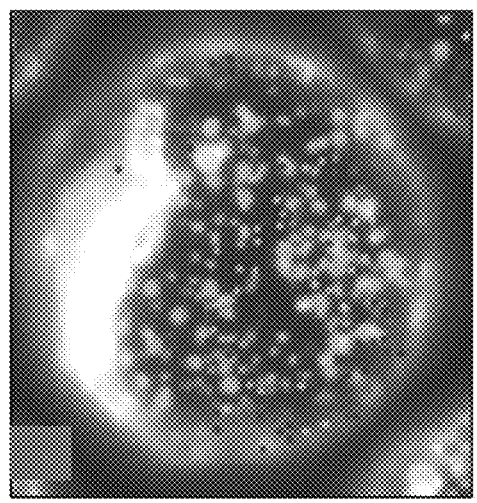
FIGS. 6A through 6C depict, respectively, in FIG. 6A) a micrograph of a complex in a micro-chamber.
Figure 6B:
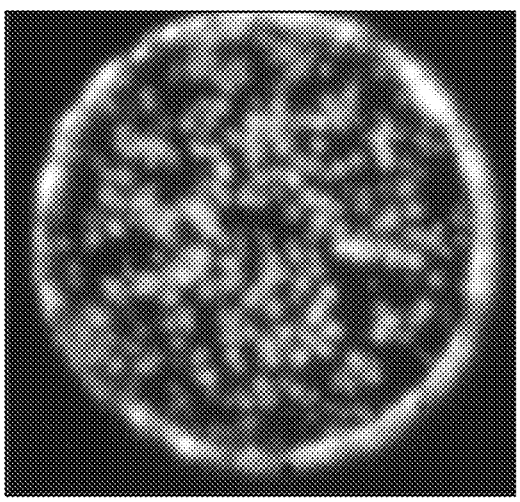
Figure 6A:
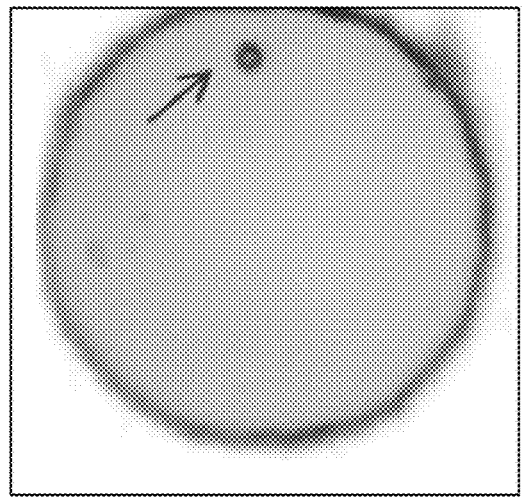

FIG. 6A is a micrograph illustrating one of the complexes inside of one of the micro-chambers.

Seeding was initiated by releasing the library fragments from the complex and clustering was performed using bridge amplification. FIG. 6B is a fluorescent micrograph of the clusters originated from the seeded libraries from the complex of FIG. 6A.

Figure 6D:
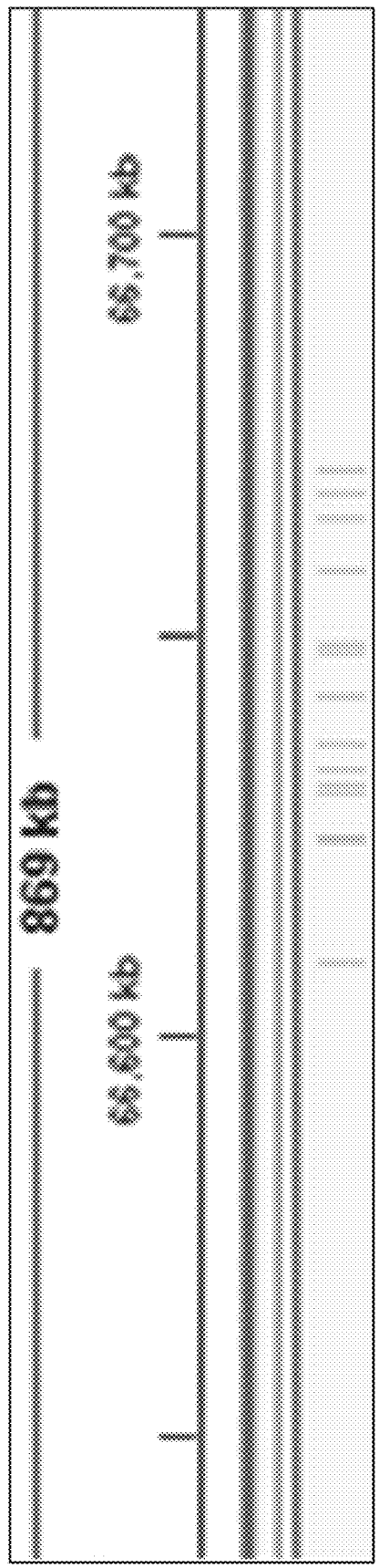
FIG. 6D illustrates an island obtained from reads from the micro-chamber shown in FIG. 6C.

First base sequencing was performed, and the real time analysis (RTA) of the micro-chamber of FIG. 6B is shown in FIG. 6C. FIG. 6D illustrates an example of the island obtained from the reads inside the micro-chamber of FIG. 6C. The results in FIG. 6D indicate that all reads originated from the same piece of long DNA fragment.

Example 2

A glass substrate with two lanes was utilized to prepare a flow cell. A hydrophobic material was deposited on the glass substrate. A positive photoresist was applied to the hydrophobic material. The positive photoresist was exposed and developed to define circular patterns outlining different micro-chambers in each of the two lanes. Any hydrophobic material beneath the non-developed resist was etched away. This exposed the surface of each micro-chamber. With the developed photoresist in place, the micro-chambers were silanized, and PAZAM was deposited thereon. Non-attached PAZAM was removed with the photoresist using a lift off technique. Then, P5 and P7 primers were grafted to the PAZAM in the micro-chambers. A lid was bonded using a UV curable adhesive to the substrate.

The micro-chambers in this example had different diameters and pitches, and were prepared in the two different lanes along the length of the flow cell. Table 1 illustrates the diameters and pitches for each of the lanes.

TABLE 1

| Flow Cell Section | 1st Section | | 2nd Section | | 3rd Section | | 4th Section | | 5th Section | |
|---|---|---|---|---|---|---|---|---|---|---|
| Lane | 1 | 2 | 1 | 2 | 1 | 2 | 1 | 2 | 1 | 2 |
| FIG. ID | (i) | (vi) | (ii) | (vii) | (iii) | (viii) | (iv) | (ix) | (v) | (x) |
| Pitch | 100 μm | 20 μm | 80 μm | 40 μm | 60 μm | 60 μm | 40 μm | 80 μm | 20 μm | 100 μm |
| Diameter | 50 μm | 10 μm | 40 μm | 20 μm | 30 μm | 30 μm | 20 μm | 40 μm | 10 μm | 50 μm |

The complexes used in this example included a solid support and sequencing-ready nucleic acid fragments attached to the solid support through an avidin-biotin linker. The library fragments of the complex were similar to those shown in FIG. 4B. The PCR free libraries were prepared in a tube following the TruSeq™ platform (Illumina, Inc.) protocol. The libraries were bound to the bead via hybridization to P7 primers, which were attached to the bead via biotin.

Figure 7A:
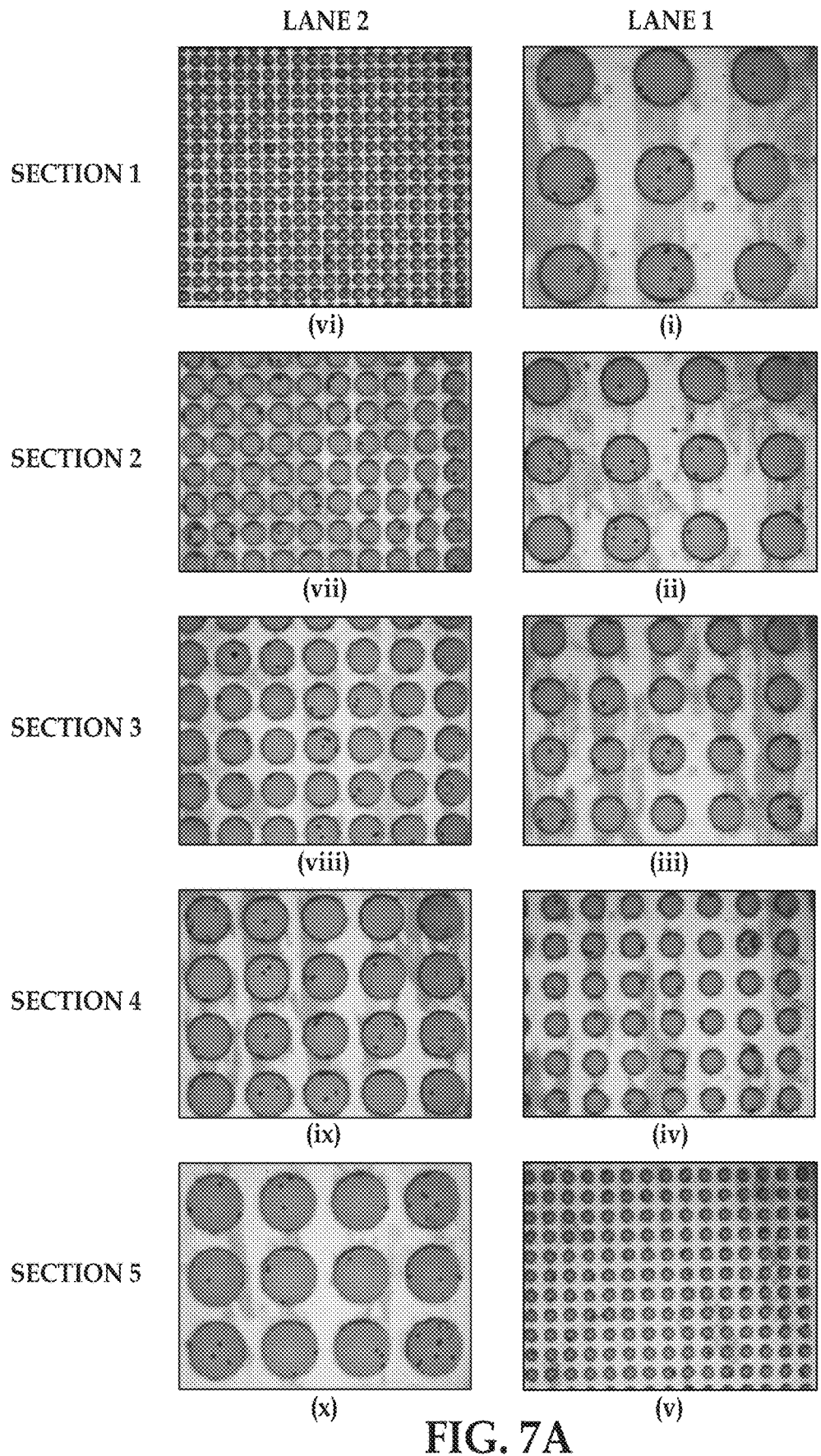
FIGS. 7A and 7B depict micrographs of portions of 5 different sections and 2 different lanes of a flow cell a) after complex introduction (FIG. 7A), and b) during real time analysis of a first base sequencing run (FIG. 7B), where the portions in sections 1-5 of lane 1 are respectively labeled (i)-(v) and the portions in sections 1-5 of lane 2 are respectively labeled (vi)-(x)

The complexes were introduced to the flow cell by flowing a hybridization buffer containing the complexes (200 μL in the hybridization buffer) through the flow cell channels. FIG. 7A is a micrograph illustrating an enlarged portion of each section of the flow cell lanes after complex introduction. The lanes and section identifications correspond with Table 1. As depicted, one or more complexes were isolated within at least some of the micro-wells.

Figure 7B:
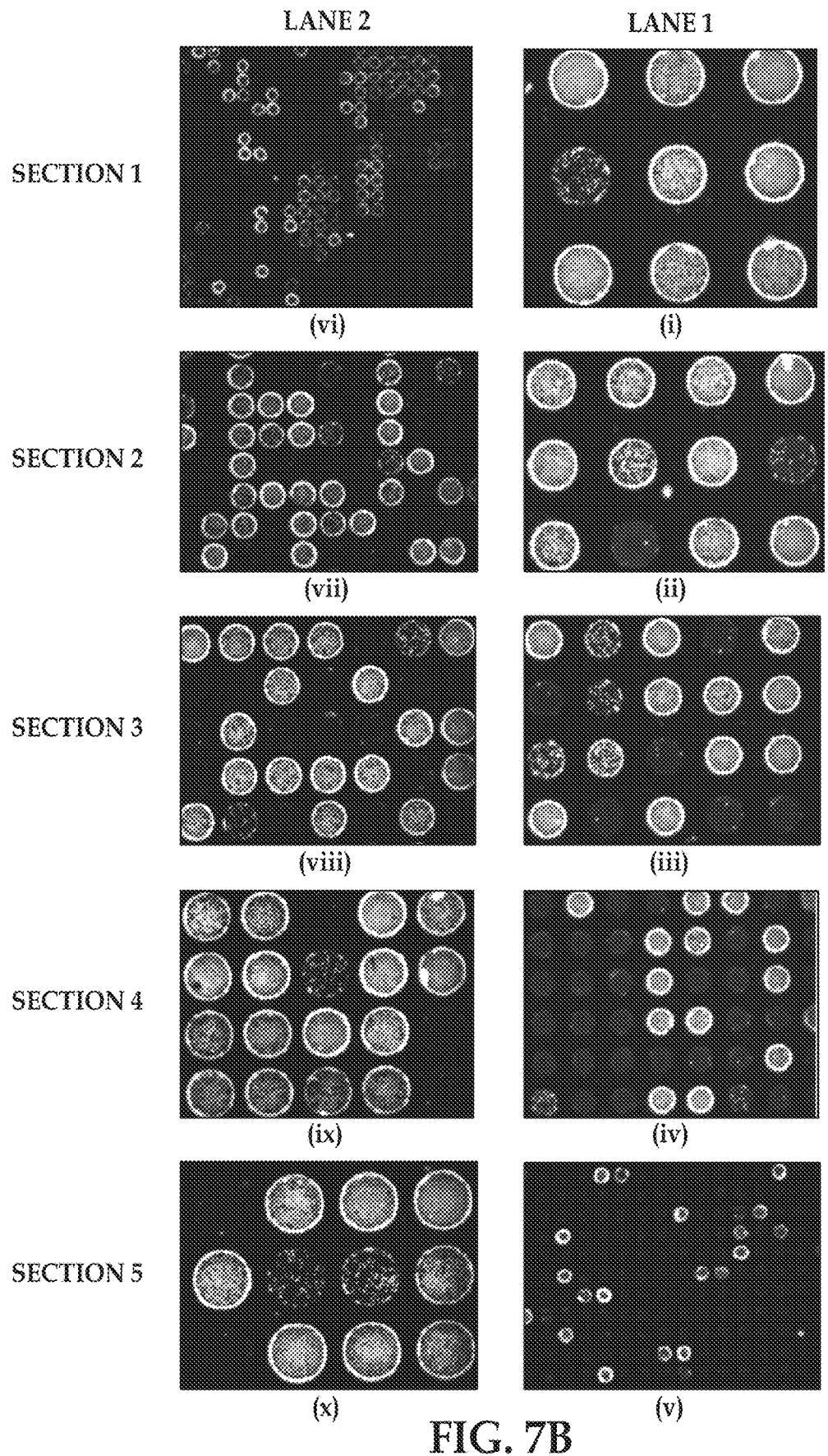

Seeding was initiated by releasing the library fragments from the complex. Library release was initiated by heating the flow cell above the melting temperature of the P7 primer. The fragments were hybridized and first strand extension was performed. The solid support and non-hybridized fragments were removed with a 0.2 M NaOH solution. Clustering was then performed using bridge amplification. First base sequencing was performed, and the real time analysis (RTA) of the micro-chambers is shown in FIG. 7B. These results illustrate that there was no cross-talk between the micro-chambers that received the complexes and those that did not receive the complexes.

Example 3

A flow cell was formed in a similar manner as described in Example 2.

Figure 8:
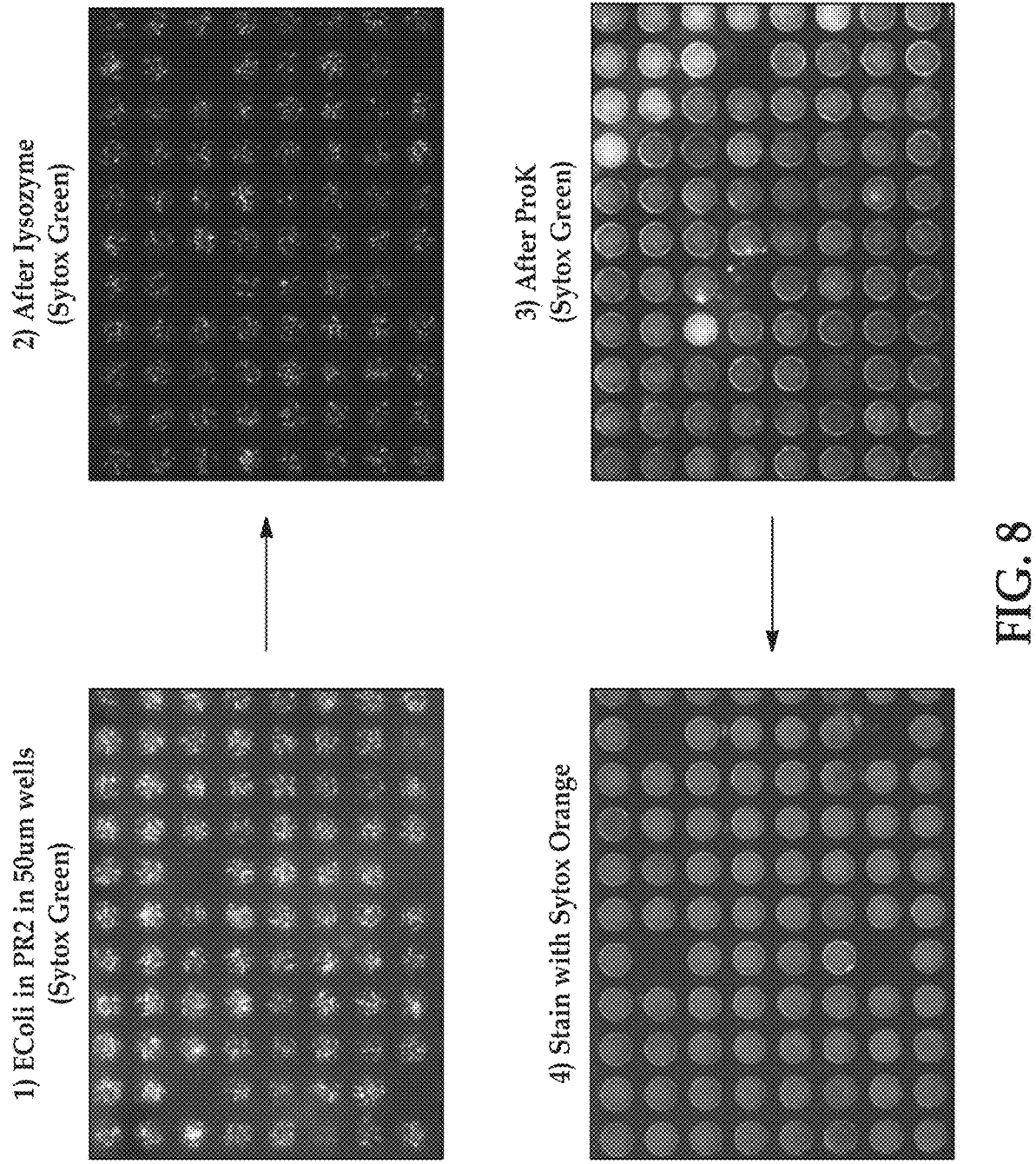
FIG. 8 illustrates several micrographs demonstrating 1) on flow cell sample encapsulation by hydrogel formation, 2) on flow cell sample lysis, 3) on flow cell DNA extraction, and 4) on flow cell library preparation.

E. Coli bacteria stained with Sytox green and dispersed in TRIS HCl wash buffer (pH 8.1) was mixed with an encapsulation matrix precursor, and was introduced into the flow cell. The flow cell was then washed. The encapsulation matrix precursor composition included acrylamide monomers, potassium persulfate (KPS), and bisacrylamide. Mineral oil containing the radical initiator (TEMED) was then introduced. The oil forced the encapsulation matrix into at least some of the micro-chambers and crosslinking was initiated. Number 1 in FIG. 8 is a micrograph of some of the micro-chambers after the hydrogel was formed. As depicted, the hydrogel was formed in most of the micro-chambers.

The hydrogel matrix allowed reagents to exchange freely in an out of the matrix, but retained the bacteria therein. To demonstrate this, a wash was performed, and then cell lysis was performed by introducing a lysozyme to the flow cell. The flow cell was heated to about 37° C. for about 30 minutes to activate the lysozyme. Number 2 in FIG. 8 is a micrograph of the micro-chambers (of number 1) after the cell lysis.

DNA extraction was performed in the presence of proteinase K (ProK), which digested contaminating proteins. Number 3 in FIG. 8 is a micrograph of the micro-chambers (of number 2) after DNA extraction.

Library preparation was performed using transposons (NEXTERA™ DNA Library Prep Kit from Illumina, Inc.) with P7-ME (mosaic end)/ME' and P5-ME/ME' adapter mixture. After tagmentation, SDS was used to remove protein and an extension reaction was performed with a PCR enzyme to create a double stranded library.

Number 4 in FIG. 8 is a micrograph of the micro-chambers (of number 3) after library preparation. These results indicate that in situ sample encapsulation and hydrogel formation may be performed on the flow cell surface.

Example 4

A glass substrate was utilized and had circular nano-depressions etched therein. CYTOP® S was used as the hydrophobic polymer (separate material 18), which was deposited across the glass substrate, including in the nano-depressions. A photoresist (Shipley S-1805) was applied to the hydrophobic polymer and developed to define a circular pattern for the hydrophobic polymer. The hydrophobic polymer was removed by plasma etching from the nano-depressions that were not covered by the photoresist. The exposed nano-depressions were then silanized and coated with the gel material. The gel material was PAZAM. A lift-off process was then used to remove the photoresist and any gel material on the photoresist. This revealed the underlying hydrophobic polymer. The hydrophobic polymer extended from about 1 μm to about 2 μm in the Z-direction above the interstitial regions. The Z-direction refers to the Z-axis of the Cartesian coordinate system for a three-dimensional space. In this example, the hydrophobic polymer defined circular shaped chambers with a diameter of 50 μm. Primer grafting was performed to attach P5 and P7 primers to the PAZAM in the nano-depressions.

Complexes similar to those shown in FIG. 4A were prepared. The fragments on a particular bead were from the same long DNA molecule. The library fragments were attached to the solid support via a desthiobiotin oligo, which has weaker affinity than biotin to the streptavidin on the bead surface. The complexes were loaded into the micro-chambers. Attachment of the complexes to the micro-chamber surface was accomplished with an anchor (e.g., complementary primers with biotin hybridized to the P5 primers attached to the gel material or alkyne-PEG-biotin linkers were covalently attached to free azides on the gel material using click chemistry). Free biotin in a saline sodium citrate buffer with sodium dodecyl sulfate was introduced and the flow cell was heated to about 80° C. to release the libraries from the respective complexes. Air was aspirated through the flow cell to push free biotin solution out. Due to the hydrophobic/hydrophilic surface structures, droplets were formed inside the micro-chambers when the liquid was pushed out by air. The droplets prevented the library fragments from diffusing to a neighboring micro-chamber.

The released library fragments were then hybridized to the surface primers in the micro-chambers, and an extension step was performed to create a complementary copy. Cluster generation was performed by bridge amplification. Sequencing was then performed on the flow cell.

Figure 9:
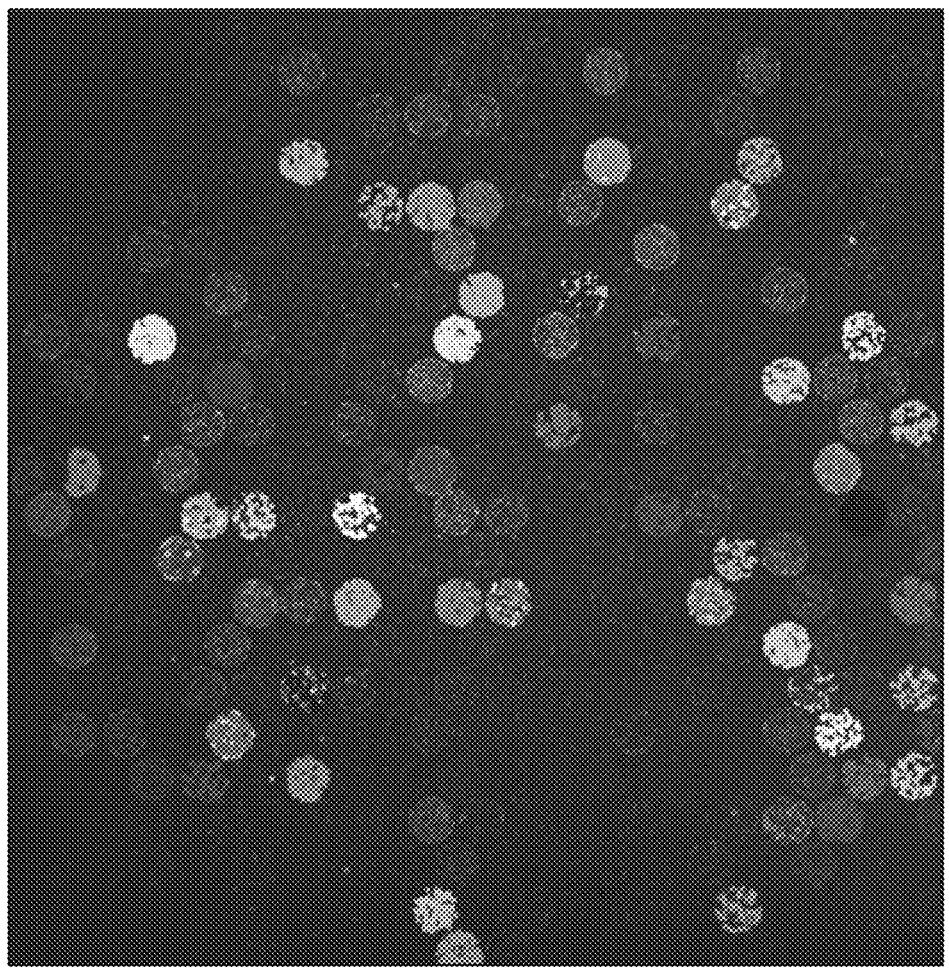
FIG. 9 is a black and white version of an originally colored fluorescence microscopy image of different micro-chambers on a flow cell after a sequencing run was performed.

FIG. 9 illustrates a portion of the flow cell after data analysis of the sequencing run. The original colors represented an island, or short reads that were grouped together based on their proximity on the reference genome. Because the respective colors were isolated to a particular micro-chamber, it was concluded that the short reads in a given micro-chamber were from the same piece of genome DNA and thus from the same complex. These results indicate that the micro-chambers were able to confine the complexes and the released library fragments within the respective chambers.

Example 5

This example illustrates on flow cell formation of a hydrogel.

A glass substrate with two lanes was utilized. Different sized micro-chambers were etched into the glass slide. The diameters and pitches for the micro-chambers in each of the lanes was the same as shown in Table 1. A hydrophobic material was deposited on the glass substrate. A positive photoresist was applied to the hydrophobic material. The positive photoresist was exposed and developed to define cover the hydrophobic material on the interstitials between the micro-chambers. Any hydrophobic material beneath the non-developed resist (and thus in the micro-chambers) was etched away. This exposed the surface of each micro-chamber. With the developed photoresist in place, the micro-chambers were silanized, and PAZAM was deposited thereon. Non-attached PAZAM was removed with the photoresist using a lift off technique. Then, P5 and P7 primers were grafted to the PAZAM in the micro-chambers. A lid was bonded using a UV curable adhesive to the substrate.

Figure 10A:
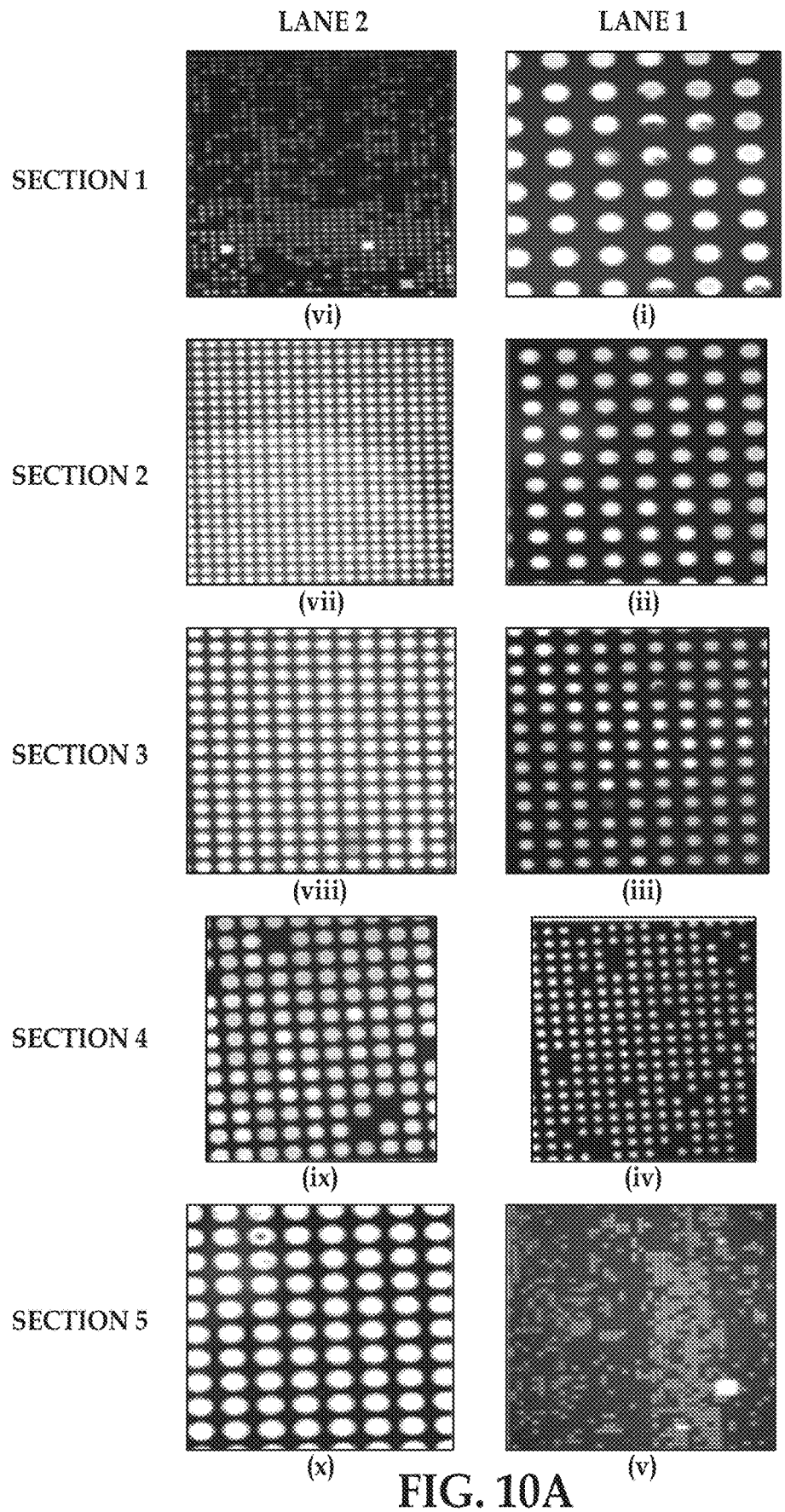
FIGS. 10A and 10B depict micrographs of portions of 5 different sections and 2 different lanes of a flow cell a) after encapsulation of an encapsulation matrix precursor (FIG. 10A), and b) after hydrogel formation (FIG. 10B), where the portions in sections 1-5 of lane 1 are respectively labeled (i)-(v) and the portions in sections 1-5 of lane 2 are respectively labeled (vi)-(x)
Figure 10B:
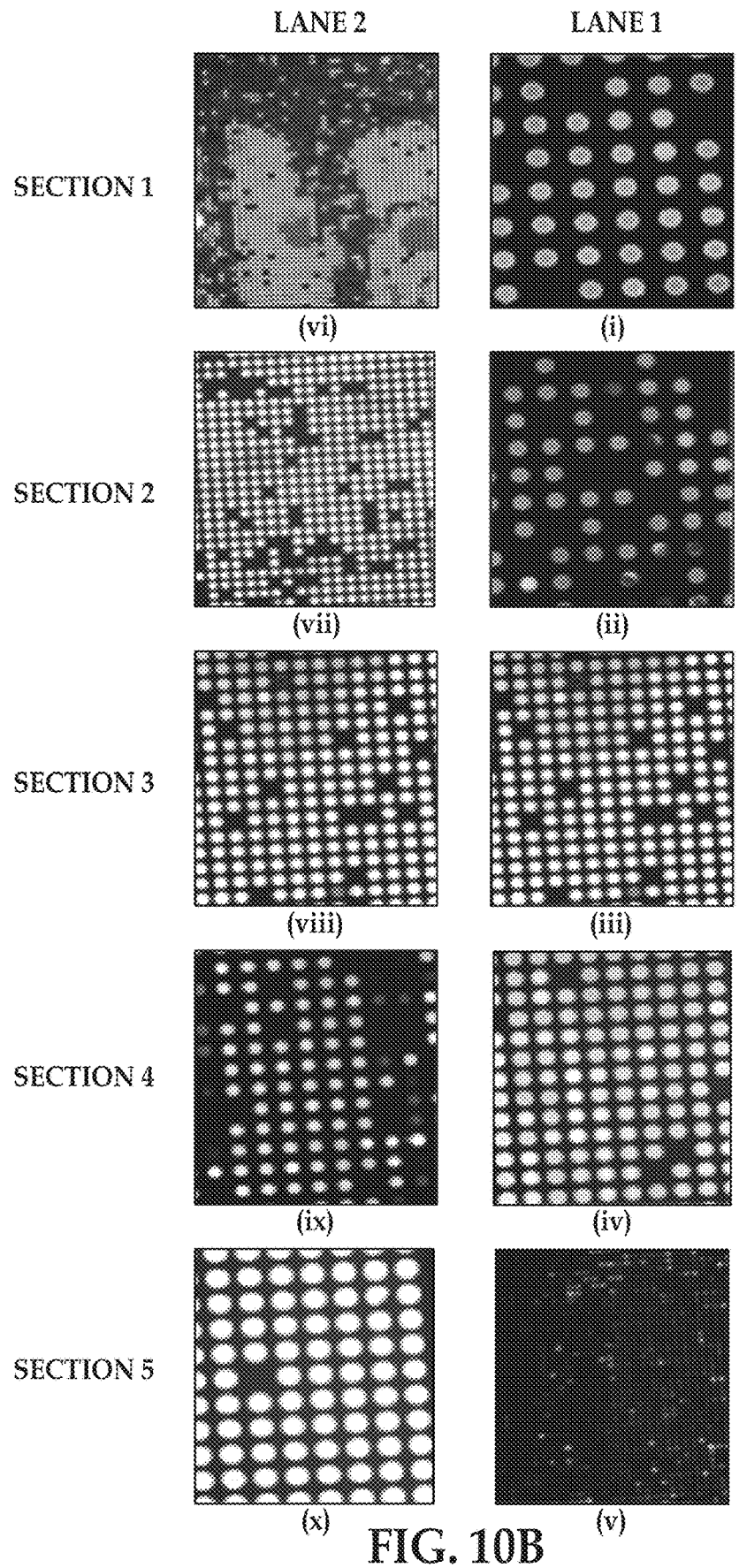

An encapsulation matrix precursor was introduced into the flow cell. The flow cell was then washed. The encapsulation matrix precursor composition included N,N'-bis(acryloyl)cystamine, acrylamide, and a 2,2'-azobis(2-methylpropionamidine) dihydrochloride. Evagreen oil was then introduced to the flow cell. The oil forced the encapsulation matrix into at least some of the micro-chambers. FIG. 10A is a micrograph of the differently sized micro-chambers (see Table 1 for diameters and pitches) in the different sections (1-5) of the 2 lanes after encapsulation. The lighter areas of each image 10A(i)-10A(x) depict the micro-chambers, and the darker areas depict the interstitials. FIGS. 10A(i)-10A(x) depict that the interstitials were relatively clear of the encapsulation matrix regardless of the size of the micro-chambers. The flow cell was then exposed to ultraviolet radiation, to initiate hydrogel formation. The flow cell was then washed with TRIS HCl wash buffer (pH 8.1). FIG. 10B is a micrograph of the differently sized micro-chambers in the different sections (1-5) of the 2 lanes after hydrogel formation. The lighter areas of each image 10B(i)-10B(x) depict the micro-chambers, and the darker areas depict the interstitials. FIGS. 10B(i)-10B(x) illustrate that a hydrogel was formed in at least some of the micro-chambers regardless of the size of the micro-chambers.

Example 6

Two single lane glass substrate flow cells were used in this example. PAZAM and P5 and P7 primers were present on the substrate surface.

Complexes similar to those shown in FIG. 4A were prepared. The fragments on a particular bead were from the same long DNA molecule. The library fragments were attached to the solid support via a desthiobiotin oligo. The complexes were loaded into the flow cell lanes. Attachment of the complexes to the lane surface was accomplished with an anchor (e.g., complementary primers with biotin hybridized to the P5 primers attached to the gel material or alkyne-PEG-biotin linkers were covalently attached to free azides on the gel material using click chemistry).

Free biotin in a saline sodium citrate buffer with sodium dodecyl sulfate was introduced into each of the flow cells. In a comparative flow cell, the buffer filled the flow channel. In an example flow cell, air at a flow rate of 100 µL/min was introduced into the flow channel to aspirate the buffer and form a shallow liquid layer around the complexes. The flow cells were heated to a temperature ranging from about 72° C. to about 77° C. to release the libraries from the respective complexes.

Images were taken of the cloud profile after library release and seeding. While not reproduced herein, these images illustrated that, when library release and seeding happened in the bulk liquid (comparative example), portions of the library departed from the solid support from which they were released and moved upward in the flow channel. These library fragments were either lost in the bulk volume or were seeded on the opposite surface of the channel from where they were released, and thus reduced the library fragment count per cloud of clusters, as well as the overall number seeded (total count=1229). In contrast, in the shallow liquid layer, all the library fragments that departed from the solid surfaces were confined by the shallow liquid layer, which resulted in more 2D localized seeding and a higher number of library fragments that were seeded (total count=2017).

The example flow cell also exhibited significantly reduced cross-surface contamination of library fragments from one surface of the flow cell to the opposite surface of the flow cell.

To test the effect of the surface density of the complexes on the droplet/puddle island/shallow liquid layer formation, 3 µm diameter streptavidin-coated magnetic beads were introduced to single lane glass substrate flow cells coated with biotin. Fluids (saline sodium citrate buffer with sodium dodecyl sulfate) with two different bead concentrations were introduced into the flow cells. One of the fluids had a higher bead concentration, about 30,000 beads/µL, while the other of the fluids had a lower bead concentration, about 6,000 beads/µL.

Figure 11A:
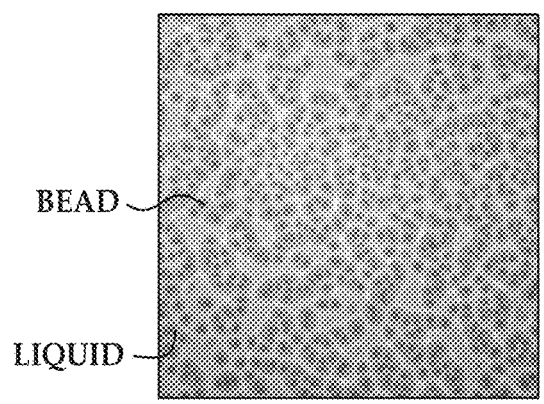
FIGS. 11A and 11B depict bright-field images of flow cell surfaces prepared with fluids having different bead concentrations and the same air-flow rate.
Figure 11B:
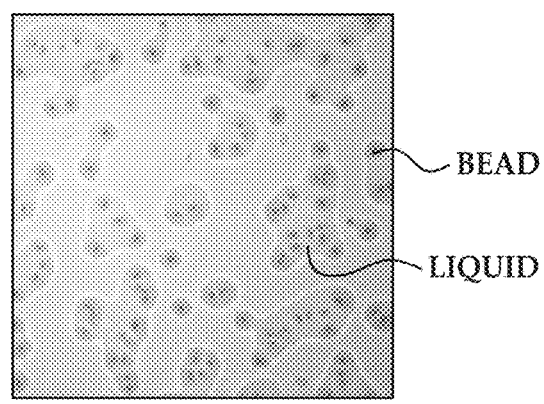

Air at a flow rate of 100 µL/min was introduced into each flow channel to aspirate the buffer and form liquid droplets around the magnetic beads. Bright-field images were taken for each of the flow cells and are shown in FIGS. 11A and 11B. FIG. 11A illustrates the flow cell surface after aspiration of the fluid with the higher bead concentration, and FIG. 11B illustrates the flow cell surface after aspiration of the fluid with the lower bead concentration.

FIG. 11A illustrates a more dense population of immobilized beads, and several puddle islands formed of contiguous droplets. FIG. 11B illustrates a less dense population of immobilized beads, and fewer puddle islands and some isolated droplets. When comparing FIG. 11A and FIG. 11B, it is clear that a greater number of beads (or complexes) on the flow cell surface enables the liquid droplets to merge and form a more uniform liquid layer across the flow cell surface.

Figure 12A:
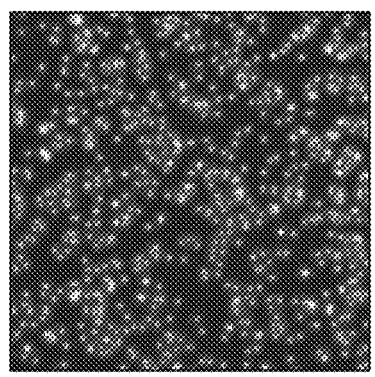
FIGS. 12A through 12E depict bright-field images of flow cell surfaces prepared with fluids having different bead concentrations and with the same air-flow rate.
Figure 12B:
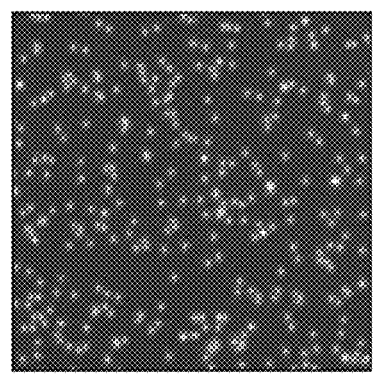
Figure 12C:
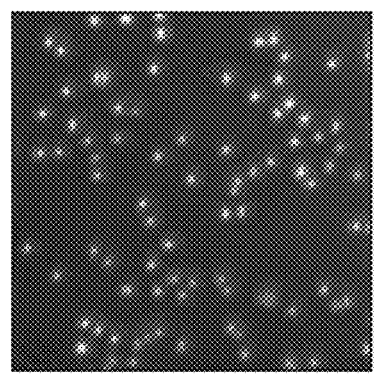
Figure 12D:
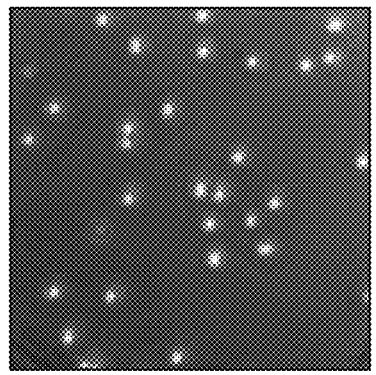
Figure 12E:
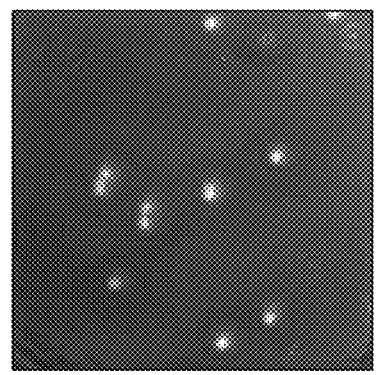

A similar experiment was performed with five fluids having different bead concentrations. The five fluids were prepared from the same initial fluid, namely a saline sodium citrate buffer with sodium dodecyl sulfate having a bead concentration of 10 mg/mL (about 700,000 beads/μL). The initial fluid was diluted differently to generate each of the five fluids, e.g., fluid 1=250× dilution, fluid 2=500× dilution, fluid 3=2,000× dilution, fluid 4=8,000× dilution, and fluid 5=32,000× dilution. Air at a flow rate of 100 μL/min was introduced into each flow channel to aspirate the buffer and form liquid droplets around the magnetic beads. Bright-field images were taken for each of the flow cells and are shown in FIG. 12A (fluid 1=250× dilution), FIG. 12B (fluid 2=500× dilution), FIG. 12C (fluid 3=2,000× dilution), FIG. 12D (fluid 4=8,000× dilution), and FIG. 12E (fluid 5=32,000× dilution). As depicted, increased surface density of the beads correlated with increased concentration of beads in the fluid. The average diameter of the fluid domain around the individual beads progressively increased as the surface density of the beads decreased, as shown in FIG. 13.

To test the effect of the air flow rate on the droplet/puddle island/shallow liquid layer formation, 3 μm diameter streptavidin-coated magnetic beads were introduced to single lane glass substrate flow cells coated with biotin. Fluids (saline sodium citrate buffers with sodium dodecyl sulfate) with different the bead concentration were introduced into the flow cells. One of the fluids had a lower bead concentration, about 7,200 beads/μL, while the other of the fluids had a higher bead concentration, about 14,100 beads/μL.

Two different air flow rates were used, namely a flow rate of 2,000 μL/min and a flow rate of 200 μL/min. Bright-field images were taken for each of the flow cells and are shown in FIGS. 14A and 14B. FIG. 14A illustrates the flow cell surface after aspiration of the fluid with the higher air flow rate, and FIG. 14B illustrates the flow cell surface after aspiration of the fluid with the lower air flow rate. When the flow rate was high (2000 μL/min), the liquid layer was more continuous as shown in FIG. 14A; whereas, when the flow rate was low (200 μL/min), the puddle islands formed that were more separated from each other.

Figure 15A:
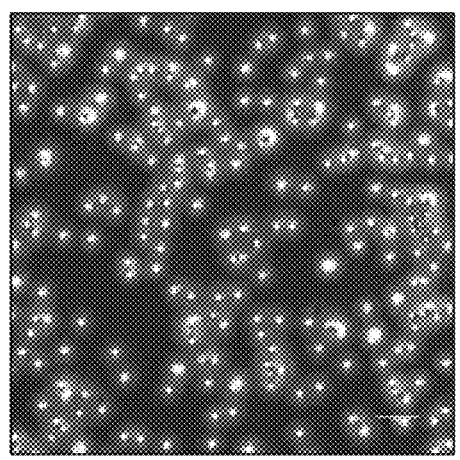
FIGS. 15A through 15D depict bright-field images of flow cell surfaces prepared with fluids having the same bead concentration and different salt concentrations and with the same air-flow rate.
Figure 15B:
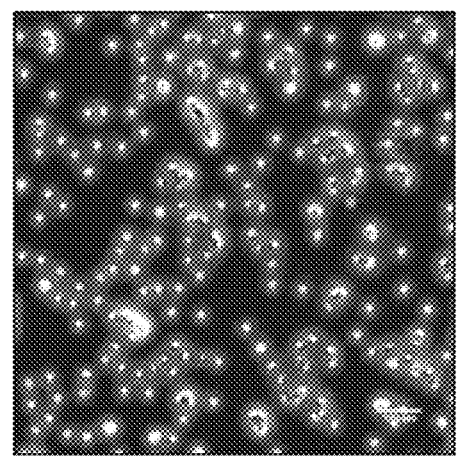
Figure 15C:
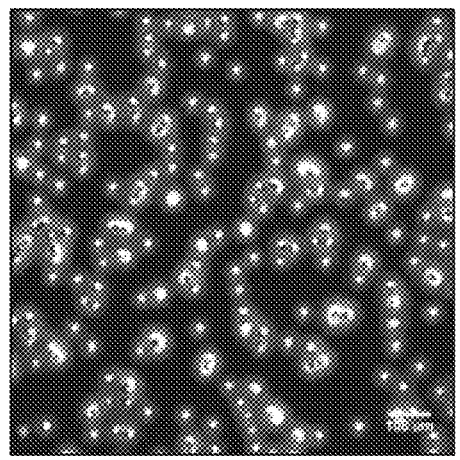
Figure 15D:
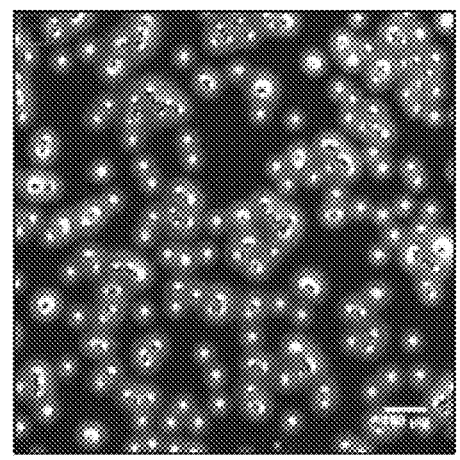
Figure 16:
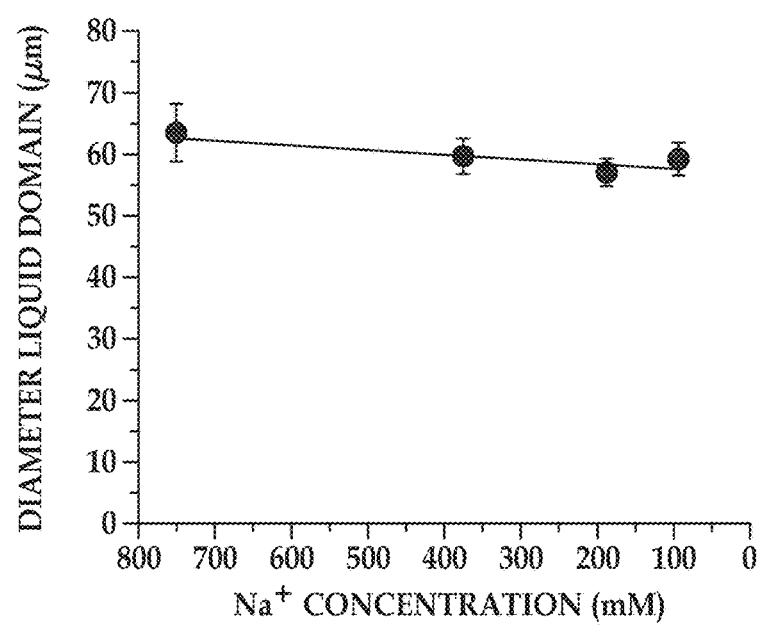
FIG. 16 is a graph of the diameter of the water domain (e.g., droplet, puddle islands, liquid layer) (in µm) versus the salt concentration (mM Na⁺), where the data was extrapolated from FIGS. 15A through 15D.

Another experiment was performed with four fluids having the same bead concentration and different salt concentrations. Each fluid was a saline sodium citrate buffer with sodium dodecyl sulfate having a bead concentration of 10 mg/mL (about 700,000 beads/μL). The sodium concentration in each solution was different, e.g., fluid 6=750 mM $Na^+$, fluid 7=375 mM $Na^+$, fluid 8=127.5 mM $Na^+$, and fluid 9=93.8 mM $Na^+$. Air at a flow rate of 100 μL/min was introduced into each flow channel to aspirate the buffer and form liquid droplets around the magnetic beads. Bright-field images were taken for each of the flow cells and are shown in FIG. 15A (fluid 6=750 mM $Na^+$), FIG. 15B (fluid 7=375 mM $Na^+$), FIG. 15C (fluid 8=127.5 mM $Na^+$), and FIG. 15D (fluid 9=93.8 mM $Na^+$). As depicted, increased salt concentration did not seem to have an effect on the liquid droplets that formed. The average diameter of the fluid domain around the individual beads remained substantially consistent (e.g., within 10 μM) across the different salt concentrations, as shown in FIG. 16.

Additional Notes

Furthermore, it is to be understood that the ranges provided herein include the stated range and any value or sub-range within the stated range, as if they were explicitly recited. For example, a range represented by from about 2 mm to about 300 mm, should be interpreted to include not only the explicitly recited limits of from about 2 mm to about 300 mm, but also to include individual values, such as about 15 mm, 22.5 mm, 245 mm, etc., and sub-ranges, such as from about 20 mm to about 225 mm, etc.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

While several examples have been described in detail, it is to be understood that the disclosed examples may be modified. Therefore, the foregoing description is to be considered non-limiting.

What is claimed is:

1. A flow cell, comprising:
   a substrate;
   a plurality of chambers defined on or in the substrate;
   a plurality of depressions defined in the substrate and within a perimeter of each of the plurality of chambers, wherein the depressions are separated by interstitial regions and wherein each of the depressions has a bottom surface;
   amplification primers attached within each of the plurality of depressions at the bottom surface; and
   a capture site located within each of the plurality of chambers.

2. The flow cell as defined in claim 1, wherein the capture site is a well that is defined in the substrate, wherein the well has an opening dimension that is larger than an opening dimension of each of the plurality of depressions.

3. The flow cell as defined in claim 2, further comprising a chemical capture agent within the well.

4. The flow cell as defined in claim 3, wherein the chemical capture agent is the capture nucleic acid that is complementary to at least a portion of a target nucleic acid or attached to a target molecule, and wherein the target molecule is a complex including a carrier and sequencing-ready nucleic acid fragments to be amplified by the amplification primers.

5. The flow cell as defined in claim 2, further comprising a capture bead within the well, wherein the capture bead is coated with a chemical capture agent selected from the group consisting of a capture nucleic acid that is complementary to at least a portion of a target nucleic acid or attached to a target molecule, a linker for a native DNA or RNA sample, a membrane binding moiety, a member of a receptor-ligand binding pair, and a chemical reagent to interact or bond with a target molecule.

6. The flow cell as defined in claim 2, wherein the chemical capture agent is selected from the group consisting of a capture nucleic acid that is complementary to at least a portion of a target nucleic acid or attached to a target molecule, a linker for a native DNA or RNA sample, a membrane binding moiety, a member of a receptor-ligand binding pair, and a chemical reagent to interact or bond with a target molecule.

7. The flow cell as defined in claim 1, wherein the capture site is a protrusion having a chemical capture agent on a surface thereof.

8. The flow cell as defined in claim 1, wherein the capture site includes a chemical capture agent positioned on a portion of the interstitial regions.

9. The flow cell as defined in claim 1, further comprising a hydrophobic material positioned on the substrate, wherein the hydrophobic material defines walls of each of the plurality of chambers.

10. The flow cell as defined in claim 1, wherein each of the plurality of chambers has a height sufficient to block lateral diffusion of released library fragments between adjacent chambers.

11. The flow cell as defined in claim 1, further comprising a polymer layer in each of the depressions, and wherein the primers are attached to the polymer layer.

12. The flow cell as defined in claim 1, wherein:
each of the plurality of chambers has an opening dimension ranging from about 1 µm to about 1000 µm;
each of the plurality of depressions has an opening dimension ranging from about 1 nm to about 2 µm; and
the chamber opening dimension is greater than the depression opening dimension.

13. The flow cell as defined in claim 1, wherein:
the plurality of chambers is arranged in a first pattern across the substrate; and
respective sub-sets of the plurality of depressions are arranged in a second pattern within in each of the chambers.

14. The flow cell as defined in claim 1, wherein the plurality of chambers is patterned into the substrate.

15. The flow cell as defined in claim 1, wherein:
the capture site is configured to localize a complex or sample; and
the amplification primers are to amplify a sequencing-ready nucleic acid fragment of the complex or a library fragment generated from the sample.

16. The flow cell as defined in claim 1, wherein the capture site is isolated from each of the plurality of depressions.

* * * * *